US010905585B1

(12) United States Patent
Sabin

(10) Patent No.: US 10,905,585 B1
(45) Date of Patent: Feb. 2, 2021

(54) RESPIRATORY THERAPEUTIC ELECTRIC HEAT SOURCE FACE MASK

(71) Applicant: Robert Sabin, Mill Neck, NY (US)

(72) Inventor: Robert Sabin, Mill Neck, NY (US)

( * ) Notice: Subject to any disclaimer, the term of this patent is extended or adjusted under 35 U.S.C. 154(b) by 0 days.

(21) Appl. No.: 16/893,212

(22) Filed: Jun. 4, 2020

Related U.S. Application Data

(63) Continuation-in-part of application No. 16/798,143, filed on Feb. 21, 2020, now Pat. No. 10,772,371.

(51) Int. Cl.
*A61F 7/12* (2006.01)
*A61M 16/06* (2006.01)
(Continued)

(52) U.S. Cl.
CPC .............. *A61F 7/12* (2013.01); *A61F 7/0085* (2013.01); *A61M 16/06* (2013.01);
(Continued)

(58) Field of Classification Search
CPC .......... A61M 16/1045; A61M 16/1075; A61M 16/108; A61M 16/1085; A61M 16/109;
(Continued)

(56) References Cited

U.S. PATENT DOCUMENTS 908,108 A 12/1908 Knudsen
2,376,348 A * 5/1945 Fox ...................... A61M 16/00 128/204.25
(Continued)

FOREIGN PATENT DOCUMENTS

CN 106582491 A 4/2017
CN 100723509 A 5/2017
(Continued)

OTHER PUBLICATIONS

Kalsarellas, MD, PhD, Dimitrios; Radbo, MD, Erik; Ben-Shabat, MD, Ilan; Matisson. MD, Jan; Bagge, MD, PhD, Roger Olofsson, "The Effect of Temperature and Perfusion Time on Response, Toxicity, and Survival in Patients with In-Transit Melanoma Metastases Treated with Isolated Limb Perfusion"; www.ncbi.nlm.nih.gov/29766389; Ann Surg Oncol. 2018;25(7):1836-1842. doi:10.1245/s10434-018-6459-9.
(Continued)

*Primary Examiner* — Michael J Tsai
(74) *Attorney, Agent, or Firm* — Alfred M. Walker; John F. Vodopia; Jennifer Yancy

(57) ABSTRACT

A therapeutic face mask apparatus for wearers with resistant respiratory viruses, is connected to a heat gun that provides adjustable heated and humidified air for inhalation. The heat gun heats ambient air that is breathed in through the face mask during normal breathing, which is worn over the nose and mouth of a person. A temperature gauge monitors temperature for future adjustment of the amount of heat generating current to raise the heat to a predetermined temperature to deactivate resistant viruses in compromised upper and/or lower respiratory systems of the wearer. The air in the chamber is heated for inhalation by a resistive element in the heat gun. The temperature of the resistive material (and by extension the warm air generated), is regulated/adjusted by increasing or decreasing the current output settings on the power source, so that heated and pressured air is produced.

21 Claims, 8 Drawing Sheets

(51) Int. Cl.

| | |
|---|---|
| ***A61M 16/10*** | (2006.01) |
| ***A61F 7/00*** | (2006.01) |
| ***A61M 16/08*** | (2006.01) |

(52) U.S. Cl.
CPC .... *A61M 16/0875* (2013.01); *A61M 16/1075* (2013.01); *A61F 2007/006* (2013.01); *A61M 2205/502* (2013.01); *A61M 2205/583* (2013.01); *A61M 2205/8206* (2013.01)

(58) Field of Classification Search
CPC .......... A61M 16/1095; A61M 2205/36; A61M 2205/362; A61M 2205/3673; A61F 7/12; A61F 7/0085; A61F 2007/006; A61F 2007/0062; A61F 2007/0055
See application file for complete search history.

(56) References Cited

U.S. PATENT DOCUMENTS

| | | | | |
|---|---|---|---|---|
| 4,245,631 | A | 1/1981 | Wilkinson et al. | |
| 4,325,365 | A | 4/1982 | Barbuto | |
| 4,601,287 | A | 7/1986 | Royce, Jr. | |
| 4,610,247 | A | 9/1986 | Stroup | |
| 4,620,537 | A | 11/1986 | Brown | |
| 4,793,343 | A | 12/1988 | Cummins | |
| 4,905,686 | A | 3/1990 | Adams | |
| 5,148,801 | A * | 9/1992 | Douwens | A61M 16/1075 128/203.16 |
| 5,255,674 | A * | 10/1993 | Oftedal | A61M 16/16 128/203.16 |
| 5,349,161 | A | 9/1994 | Bockholt | |
| 5,511,541 | A | 4/1996 | Dearstine | |
| 5,706,802 | A | 1/1998 | McCormick | |
| 5,749,704 | A | 5/1998 | Jerdee | |
| RE36,165 | E | 3/1999 | Behr | |
| 6,196,221 | B1 | 3/2001 | McCormick | |
| 6,584,972 | B2 * | 7/2003 | McPhee | A61M 16/0841 128/203.17 |
| 6,868,852 | B2 | 3/2005 | Gaschke | |
| 7,615,049 | B2 | 11/2009 | West et al. | |
| 7,845,351 | B2 | 12/2010 | Mathis et al. | |
| 8,328,859 | B2 | 12/2012 | Hansen et al. | |
| 8,733,357 | B2 | 5/2014 | Sullivan, Jr. | |
| 10,194,971 | B2 | 2/2019 | Wegrzyn, III | |
| 10,201,198 | B2 | 2/2019 | Tong et al. | |
| 2003/0221688 | A1 * | 12/2003 | Carey | A61M 16/06 128/200.24 |
| 2005/0150501 | A1 * | 7/2005 | Opitz | A61M 16/108 128/207.18 |
| 2008/0149100 | A1 * | 6/2008 | Van Holst | A61M 16/1075 128/204.17 |
| 2009/0107982 | A1 * | 4/2009 | McGhin | A61M 16/1095 219/497 |
| 2010/0242964 | A1 | 9/2010 | Reynolds | |
| 2011/0253136 | A1 * | 10/2011 | Sweeney | A61M 16/161 128/203.12 |
| 2011/0207152 | A1 | 12/2011 | Duveen et al. | |
| 2011/0297152 | A1 | 12/2011 | Duveen et al. | |
| 2013/0032148 | A1 * | 2/2013 | Neely | A61M 16/0694 128/204.18 |
| 2015/0173445 | A1 | 6/2015 | Gordon et al. | |
| 2015/0230524 | A1 | 8/2015 | Stevens et al. | |
| 2018/0078798 | A1 | 3/2018 | Fabian et al. | |
| 2019/0083395 | A1 * | 3/2019 | Doshi | A61M 15/0003 |
| 2019/0209801 | A1 * | 7/2019 | Kimble | A61M 16/0666 |
| 2019/0335817 | A1 * | 11/2019 | Freeman | A24F 47/008 |
| 2020/0206442 | A1 * | 7/2020 | Knepper | A61M 16/0616 |

FOREIGN PATENT DOCUMENTS

| | | | |
|---|---|---|---|
| CN | 208016956 | U | 10/2018 |
| CN | WO2019043118 | A1 | 3/2019 |
| CN | 209749876 | U | 12/2019 |
| DE | WO2019081034 | A1 | 5/2019 |
| KR | 20110050897 | A | 5/2011 |
| KR | WO2015167098 | A1 | 11/2015 |
| KR | WO2018097507 | A1 | 5/2018 |

OTHER PUBLICATIONS

Emma(Sunrise Specialty Staff); "Ideal Sauna Temperature: How Hot is Your Sauna?"; https://www.sunrisespecialty.com/sauna-temperature.

Peddie. Sandra. "Researchers: Far-UVC light kills virus without skin or eye damage": Newsday; updated May 1, 2020; https://www.newsday.com/news/health/coronavirus/coronavirus-ultraviolet-airborne-1.44287805.

Rickaby. PhD, David A.; Fehring. BS, Jeffrey F.; Johnston, MD, Micheal R.; Dawson, PhD, Christopher A.; "Tolerance of the isolated perfused lung to hyperthermia"; Journal of Thoracic and Cardiovascular Surgery; vol. 101, No. 4, Apr. 1991; pp. 732-739.

"Respiratory Tract": Wikipedia: http://en.wikipedia.org/w/index.php/titie=Respiratory_tract&oldid=947647430I last edited Mar. 27, 2020.

"Can Sauna Kill Coronavirus? What We Know About Sauna and Coronavirus"; 2019; https:saunamarketplace.com/can-sauna-kill-coronavirus.

"Gerbing 12V 10AH Muli-Volt Heated Clothing Battery Kit"; The Warming Store; http://www.thewarmingstores.com/gerbing-heated-clothing-12v-muiti-volt-battery-kit.html.

"Peek (Polyetheretherketone)—Bearing Grade"; http://sterlingplasticsinc.com/materials/peek-polyetheretherketone-bearing-grade; 2012.

"Upper respiratory tract": Medline Plus Medical Encyclopedia; last updated Apr. 11, 2020; Nat'l Institutes of Health, US Dept of Health & Human Services, US Nat'l Library of Medicine, Bethesda, MD.

"Finnish Sauna"; Wikipedia; http://en.wikipedia.org/wiki/Finnish_sauna.

First data on stability and resistance of SARS coronavirus compiled by members of WHO laboratory network; May 4, 2003; htps://www.who.int/csr/sars/survival_2003_05_04/en/.

"Coronavirus": Wikipedia; last edit May 29, 2020: https://en.wikipedia.org/wiki/Coronavirus.

"Lung Diseases"; National institute of Environmental Health Sciences; Your Environment Your Health; last reviewed Jan. 2, 2020; https://www.niehs.nih.gov/health/topics/conditions/lung-disease/index.cfm.

"Heat to Kill Coronavirus"; Apr. 8. 2020, ConsumerLab.com.

"Warm & Safe Battery 7.4 Volt5 7.8 Amp"; The Warming Store; Apr. 8, 2020; https://www.thewarmingstore.com/warm-n-safe-battery-7-4-volt-7-8-amp.

"Peek"; Curbell Plastics; May 29, 2020: https://www.curbellplastics.com/Research-Solutions/Materials/PEEK.

"What Does Coronavirus Do to Your Body?"; WebMD Lung Disease & Respiratory Health—Coronavirus; reviewed by Brunilda Nazario. MD, Apr. 3, 2020.

Gale, Jason; "There is a 'Tipping Point' Before Coronavirus Kills"; Bloomberg Businessweek; Mar. 8, 2020; https://www.bloomberg.com/news/articies/2020-03-08/coronavirus-nears-fatal-tipping-point-when-lungs-are-inflamed.

Belluck, Pam; "What Does the Coronavirus Do to the Body?"; The New York Times, Mar. 26, 2020; https://www.nytimes.com/article/coronavirus-body-symptoms.html.

Roberge, Raymond J.; Bayer, Emily; Powell. Jeffrey B.; Coca, Aitor; Roberge, Marc R.; Benson, Stacey M.; "Effect of Exhaled Moisture on Breathing Resistance of N95 Filtering Facepiece Respirators": published Jun. 3, 2010; Oxford University Press on behalf of the British Occupational Hygiene Society; Ann Occup Hyg. 2010;54(6):671- 677; doi:10.1093/annhyg/meq042.

"The Solution for Osmosis Problems"; HOTVAC-Hull Cure; www.hotvac.com/fa/default.aspx; downloaded Apr. 20, 2020.

"Don't Sweat It! These 4 High Temp Plastics Can Take the Heat"; Craft Industries; https://www.craftechind.com/dont-sweat-4-high-temp-plastics-can-take-heat/; downloaded May 30, 2020.

(56) References Cited

OTHER PUBLICATIONS

David C. Koch Regional Perfusion Cancer Therapy Center web page; UPMC/Hillman Cancer Center; https://hillman.upmc.com/cancer-care/surgical-oncology/koch-regional-cancer-therapy-center; downloaded Apr. 21, 2020.
"YSK: What is the highest temperature a human being can survive"; reddit.com—Health & Sciences; https://www.reddit.com/r/YouShouldKnow/comments/6kete0/ysk_what_is_the_highest_temperature_a_human_being/; downloaded May 30, 2020.
O'Brien, Rebecca Davis; "Doctors Are mprovising Coronavirus Treatments, Then Quickly Sharing Them"; The Wall Street Journal; Apr. 9, 2020.
Wagner HT4500 Heavy-Duty Heat Tool Set: https://www.homedepot.com/p/Wagner-HT4500-Heavy-Duty-Heat-Tool-Set; downloaded May 29, 2020.
Steinel HG2520E Professional Heat Gun; http://www.steinel.net/HG_2520_E; downloaded May 30, 2020.
Ryobi 18-Volt ONE+ Lithium-Ion Cordless Heat Gun; https://www.homedepot.com/p/RYOBI-18-Volt-ONE-Lithium-Ion-Cordless-Heat-Gun-Tool-Only-P3150/306925921; downloaded May 18, 2020.
Master Proheat Heat Gun; Instruction Manual 2020; Master Appliance Corp.; Racine, WI.
Chan, K.H., Peiris, J.S. Malik, Lam, S.Y., Poon, L.L.M., Yuen, K.Y., Seto, W.H.; "The Effects of Temperature and Relative Humidity on the Viability of the SARS Coronavirus": Advances in Virology; Hindawi Publishing Corporation; vol. 2011. Article ID 734690.
"Air Purifying Smart Electric Face Mask, Style 1/2": Internet; https//geek.wish.com/product; downloaded Mar. 22, 2020.
"Psolar.Ex Cold Weather Face Mask"; Internet; https://www.exmask.com/index.php; downloaded Mar. 22, 2020.
"Electric Heated Thermal Warm Face Mask"; internet; https://heatedsockz.com/products; downloaded Apr. 20, 2020.
"The Subzero Warm Breath Mask"; internet, https://www.hammacher.com/product; downloaded Apr. 21, 2020.
"Heated Air Runner's Mask": Internet; http:www.halfbakery.com/idea/Heated_20Air_20Runner_27s_20Mask; downloaded Apr. 21, 2020.
"N-Ferno(R) 6970 Extreme Balaclava Face Mask w/ Hot Rox (TM)"; internet; https://ww.ergodyne.com; downloaded Apr. 21, 2020.
"2200N95 Series Particulate Respirator"; internet; https://www.moldex.com/poduct/2200-n95-series-respirator; downloaded Apr. 21, 2020.
John G. Seifert, PhD; "The Cardiopulmonary Effect of a Heat and Moisture Exchange Mask on COPD Patients 38 During Cold Exposure"; submitted Jun. 2009; Movement Science/Human Performance Laboratory, MSU, Bozeman, MT.
"DIY Carbon Tape Heated Gloves V2.0": ShenzhenVisit My SiteIFollow; internet; http://www.instructables.com/id/DIY-carbon-heated-gloves, downloaded Mar. 22, 2020.
"Gerbing Gyle 7V 7000mAh Extended-Life Battery with Remote & Charger Kit"; internet; https://www.thewarmingstore.com/gerbing-extended-life-battery-with-Remote; downloaded Mar. 22, 2020.
"EeonTex Conductive Fabric—COM-14110"; internet, https://www.sparkfun.com/products/14110; downloaded Mar. 22, 2020.
Da Beuther, RJ Martin; "Efficacy of a heat exchanger mask in cold exercise-induced asthma"; Abstract; May 2006; National Center for Biotechnology Information: pp. 1188-1193; https://www.ncbi.nlm.nih.gov/pubmed/16685008.
"Sleep Apnea Statistics"; The Sleep Zone; Cheap CPAP Supplies Blog; Feb. 9, 2018; internet: http://www.cheapcpapsupplies.com/blog/sleep-apnea-statistics.
"Cold Weather and Your Lungs"; American Lung Association; Jan. 4, 2018; https://www.lung.org/about-us/media/top-stories/cold-weather-your-lungs.
"Lung Diseases—Introduction"; last review Jan. 2020; National Institute of Environmental Health Sciences; https://www.niehs.nih.gov/health/topics/conditions/lung-disease/index.cfm.
"Asthma Facts"; United States Environmental Protection Agency; May 2018; EPA-402-F-04-019.
"AirGuard Medical CT Cold Air Winter Face Mask"; https://www.the-perfect-present.com/airguard-medical/ct-mask.html; downloaded Mar. 22, 2020.
Laura Johannes; "A Breath of Warm Air on a Cold Day"; updated Feb. 16, 2010; The Wall Street Journal.
Rodrigo Athanazio; "Airway disease: similarities and differences between asthma, COPD and bronchiectasis"; CLINICS; Sep. 27, 2012; Hospital das Clínicas da Faculdade de Medicina da Uníversidade de São Paulo, Heart Institute (InCor), Pulmonary Division, São Paulo/SP, Brazil.
"ColdAvenger Classic Fleece Cold Weather Face Mask"; internet; https://www.amazon.com/ColdAvenger-Classic-Fleece-Cold-Weather-Face-Mask; downloaded Mar. 23, 2020.
"ColdAvenger Cold Weather Face Masks—Catalog"; internet; https://coldavengercom; downloaded Feb. 1, 2020.
"Asthma Facts"; AAFA.org., Medical Review, Feb. 2018, updated Jun. 2019; https://www.aafa.org/asthma-facts; Asthma and Allergy Foundation of America, Arlington, VA 22202.
"National Facts on Asthma", Asthma Fact—CDC's National Asthma Control Program Grantees; Jul. 2013; The Centers, For Disease Control and Prevention; Atlanta, GA.
Maria D'Amato, Antonio Molino, Giovanna Calabrese, Lorenzo Cecchi, Isabella Annesi-Maesano, Gennaro D'Amato; "The impact of cold on the respiratory tract and its consequences to respiratory health"; Clinical and Translational Allergy 8, 20 (2018); https://doi.org/10.1186/s13601-018-0208-9.
John G Seifert, Jeremy Frost, John A St Cyr; "Recovery benefits of using a heat and moisture exchange mask during sprint exercise in cold temperatures"; Oct. 11, 2017; SAGE Open Medicine, vol. 5; pp. 1-6; sagepub.co.uk/journals.
Doug Dunlop; Heat Exchanger Masks—A Love Story; Coldbike BLog; Feb. 13, 2019; internet; https://www.coldbike.com/2019/02/13/heat-exchanger-masks-a-love-story.
Gadi Borkow, Steve S Zhou, Tom Page, Jeffrey Gassay: "A Novel Anti-Influenza Copper Oxide Containing Respiratory Face Mask"; PLoS One, vol. 5, Issue 6, e112955, published Jun. 25, 2019; www.plosone.org.
www.carbonheater.us; "About Carbon Fiber Tape & Carbon Fiber Rope"; Feb. 7, 2020.
www.carbonheater.us; "Check out Carbon Tape"; Feb. 11, 2020 (#1).
www.carbonheater.us; "Check out Carbon Tape"; Feb. 11, 2020 (#2).
www.instructables.com; You Can Do It; Feb. 11, 2020.
"AirFit (TM) F20 Full Face CPAP/BiLevel Mask with Headgear"; https://www.cpapxchange.com/resmed-airtouch-f20-full-face-cpap-bilevel-mask.html; downloaded Apr. 22, 2020.
Alexandra Gerea; "How hot is a sauna, and other steamy facts"; Jul. 19, 2017; https://www.zmescience.com/other/feature-post/how-how-is-sauna-19072017.
"ResMed AirFit (TM) F20, AirTouch (TM) F20 User Guide"; ResMed Pty Ltd. Bella Vista NSW 2153, Australia; ResMed.com.
"ResMed ClimateLineAir (TM) User Guide"; ResMed Ltd., Bella Vista NSW 2153, Australia; ResMed.com.
"Know your CPAP humidifier"; ResMed Blog: Manual mode: Know your CPAP humidifier—Sleep Apnea; https://www.resmed.com/en-us/sleep-apnea/sleep-blog/manual-mode-know-your-cpap-humidifier.
Zheng, Andrew; Wong, Himtang; "Temperature of a Sauna"; The Physics Factbook; ed. Glenn Elert; http//hypertextbook.com/facts/2005/HimtangWong.shtml.
Wilson, Mark; "Ford kills COVID-19 with ingenious car heater hack"; Fast Company Newsletter; May 29, 2020; https//www.fastcompany.com/9051004/ford-kills-covid-19-with-ingenious-car-heater-hack.
Kampf, G., et al; "Inactivation of coronaviruses by heat": Journal of Hospital Infection; Mar. 25, 2020: https:/dot.org/10,1016.
Conti, C., DeMarco, A.; Mastromarino, P., Tomao, P., Santoro, M.G.; "Antiviral Effect of Hyperthermic Treatment in Rhinovirus Infection"; Accepted Feb. 4, 1999; Institute of Microbiology, School of Medicine, University "La Sapienza," 00185, Rome, and Department of Biology, University of Rome Tor Vergata and Institute of Experimental Medicine, CNR, 00133 Rome, Italy.

(56) References Cited

OTHER PUBLICATIONS

Boloker, Gabrielle, Wang, Cong, Zhang, Jianrong; "Updated statistics of lung and bronchus cancer in United States"; Editorial; Journal of Thoracic Disease; 2018; jtd.amegroups.com: 10(3):1158-1161.

Boloker, Gabrielle, Wang, Cong, Zhang, Jianrong; "Erratum to updated statistics of lung and bronchus cancer in United States (2018)"; Editorial; Journal of Thoracic Disease; 2019; jtd.amegroups.com; 11(3):E63.

Abraham, John P; Plourde, Brian D; Cheng, Lijing; "Using heat to kill SARS-CoV-2"; Rev Med Virol. 2020; https://doi.org/10.1002/rmv.2115.

Cohen, Marc; "Turning up the heat on COVID-19: heat as a therapeutic intervention [version 2; peer review: 2 approved]"; first published Apr. 24, 2020; F1000Research 2020, 9:292; https://doi.org/1-12688/f1000research.23299.2.

Rivas, Kayla; "Will heated face masks kill coronavirus? Researchers testing prototype, university says"; Oct. 25, 2020; https://www.foxnews.com/health/heated-face-masks-coronavirus-researchers-testing-prototype-university.

Faucher, Samuel; Lundberg, Daniel James; Xinyao, Anna Lian; Xiaojia, Jin; Phillips, Rosalie; Parvis, Dorsa; Buongiorno, Jacopo; Strano, Michael S.; "A Virucidal Face Mask Based on the Reverse-flow Reactor Concept for Thermal Inactivation of SARS-CoV-2"; arXivLabs; Oct. 21, 2020; https://arxiv.org/abs/2010.11336.

Knio, Ziyad O; Shelton, J. Alan; O'Gara, Tadhg; "Heated Air Delivery by Micro-Sauna: An Experimental Treatment Prototype Concept for Coronavirus Disease 2019"; Cureus Inc.; accepted May 16, 2020; 12(5):e8162; doi:10.7759/cureus.8162.

Godoy, Maria; "How COVID-19 Kills: The New Coronavirus Disease Can Take a Deadly Turn"; NPR Feb. 14, 2020 Interview; Goats and Soda, NPR wshu/Public Radio; https;//www.npr.org/transcripts/805289669.

Hackett, Don Ward; "BiPap and CPAP Machines Helping COVID-19 Patients Breathe Better"; Mar. 31, 2020; https://www.precisionvaccinations.com/sleep-apnea-bipap-and-cpap.

Hackett, Don Ward; "CPAP Machines Embraced for COVID-19 Patients"; Mar. 23, 2020; https://precisionvaccinations.com/continuous-positive-airway.

Alviset, Sophie, Riller, Quentin; et al.; Continuous Positive Airway Pressure (CPAP) face-mask ventilation is an easy and cheap option to manage a massive influx of patients presenting acute respiratory failure during the SARS-CoV-2 outbreak: A retrospective cohort study; National Center for Biotechnology Information, Bethesda, MD; PLoS One. Oct. 14, 2020; 15(10):e0240645. doi: 10.1371/journal.pone.0240645. PMID: 33052968; PMCID: PMC7556440.

Lance, MD, Colleen G; "Positive airway pressure: Making an impact on sleep apnea"; Cleveland Clinic Journal of Medicine; Sep. 2019; vol. 86, Supplement 1; pp. 26-33.

American Heart Association; "Oxygenation and Ventilation of COVID-19 Patients, Module 2: Airway Management"; American Heart Association, Dallas, TX; 2020.

Shelton, Alan, O'Gara, Dr. Tadhg; "Micro-Sauna—Experimental Treatment Prototype Concept for COVID 19"; #MIXXERFIGHTSCOVID; YouTube video transcript; Apr. 7, 2020; https://www.youtube.com//watch/?v=o6lex4NsRv4.

Mixxer Makerspace; "Micro-Sauna Prototype"; Apr. 7, 2020; https://wsmixxer.org/micro-sauna/.

Cohen, Marc; Turning up the heat on COVID-19: heat as a therapeutic intervention; F1000 Research, Apr. 24, 2020, 9:292.

* cited by examiner

Fig. 6A
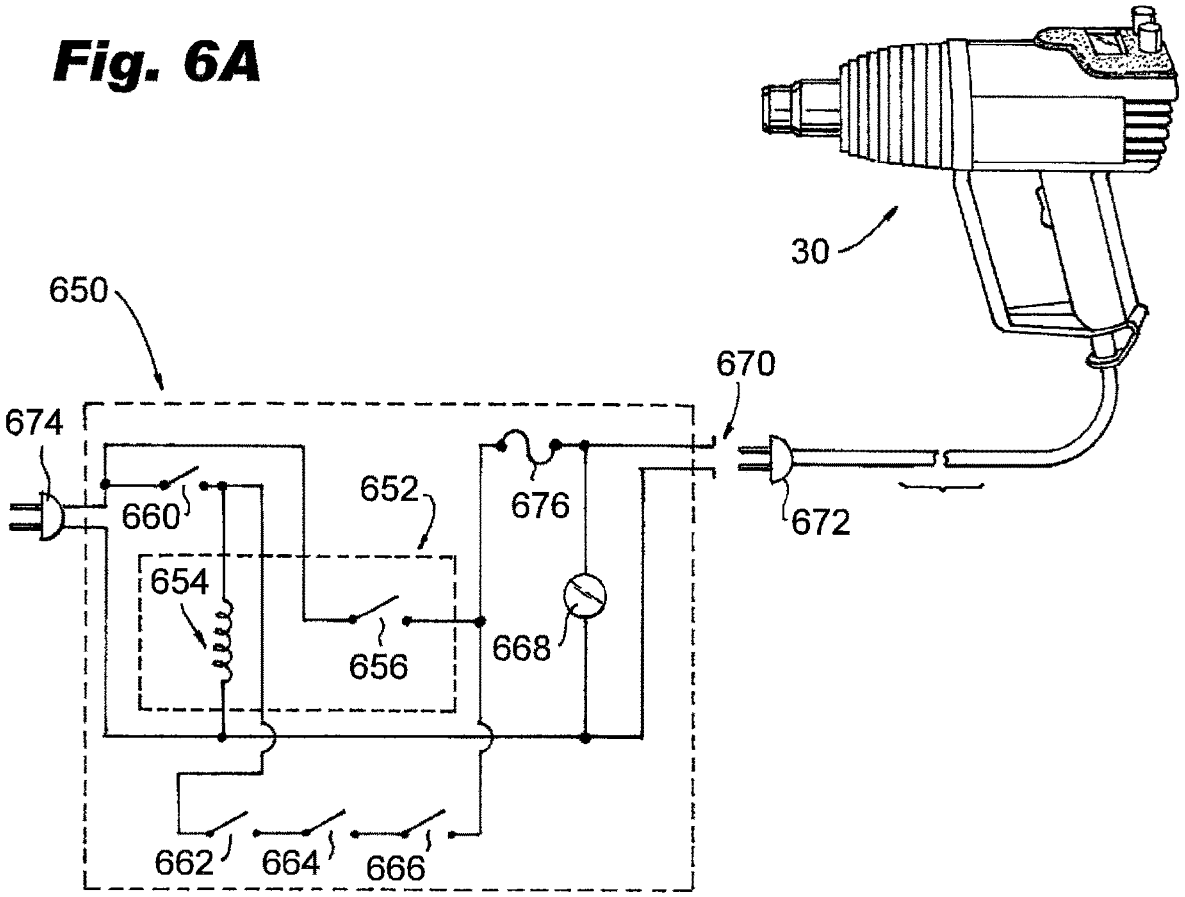
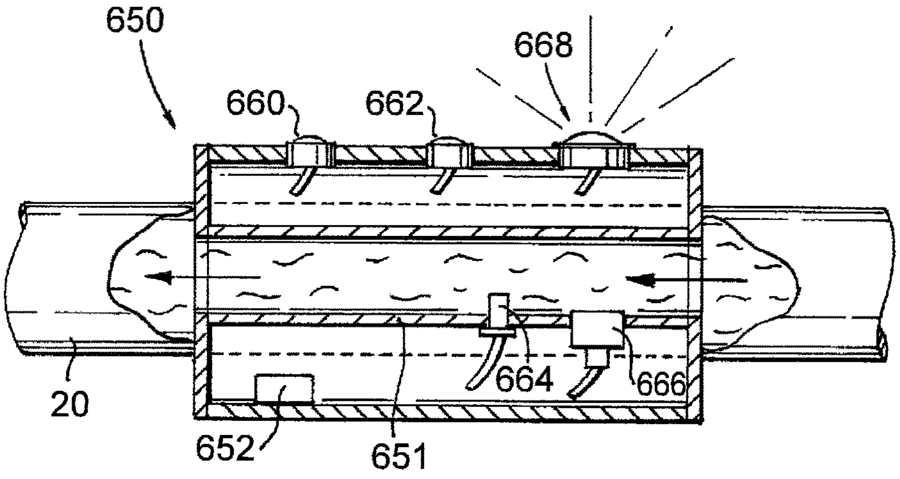
Fig. 6B

RESPIRATORY THERAPEUTIC ELECTRIC HEAT SOURCE FACE MASK

FIELD OF THE INVENTION

This invention relates to a face mask and method for using a face mask and heat source, to condition air drawn into the face mask before it is actually breathed and thereby supply heated or elevated higher temperature at a therapeutic air pressure to persons in need thereof, particularly to maintain a wearer's upper respiratory system at a further elevated high temperature, capable of inactivating viruses, such as the Coronavirus 2 (SARS CoV-2 virus), killing bacteria, fungi, tumor cells, pre-malignant cancer cells, dysplasia cells and other pathogens, and to promote an immune-stimulatory response and to prevent or inactivate a virus in the respiratory system of the wearer of the heated face mask, in both ambulatory and hospitalization settings.

BACKGROUND OF THE INVENTION

All references are included in their entirety as if reproduced in full herein.

The Center for Disease Control and Prevention (CDC) discloses that "Chronic lower respiratory diseases" are the 4th leading cause of death in the United States in 2018. Dry cold air can irritate the airways of people with asthma, CDC discloses in excess of 25 million Americans have asthma. See NIH, NIEHS, "Lung Diseases", revised 2020. Moreover, there are many patients with lung cancer, heart disease, and other diseases and irritations of the lung and airways, or any respiratory condition, who are in need of a safe, temperature adjustable, cost-effective, portable, non-burdensome intervention to warm cold inhaled air and all other air, and to humidify said air. Sleep Apnea statistics show that the current population of the United States is 326 million, 10% of which have mild obstructive sleep apnea. This translates to 32.6 million people who could possibly benefit from Applicant's invention. Moreover, there are an estimated 22 million Americans who suffer from moderate to severe sleep apnea, many of these who could benefit from Applicant's invention. People with cardiac conditions also could benefit from Applicant's invention. See "The Sleep Zone", "Sleep Apnea Statistics" Feb. 9, 2018. See also US EPA, "Asthma continues to be a serious public health problem in the United States", EPA-402F-04-019, May 2018.

Air Guard discloses some, but not all, of the people who could benefit from the inhalation of warm, humidified air. The medical costs caused by cold dry air is in the many billions. The suffering is incalculable. See The-perfect-present.com, "Air Guard Medical CT Cold Air Winter Face Mask", website, 2019.

"THE CARDIOPULMONARY EFFECT OF A HEAT AND MOISTURE EXCHANGE MASK ON COPD PATIENTS DURING COLD EXPOSURE" by John G. Seifert, PhD June 2009, discloses a mask that works in the COPD patient during cold exposure. Siefert discusses "Recovery benefits of using a heat and moisture exchange mask during sprint exercise in cold temperatures" which discloses that an HME (Heat and moisture exchange masks) mask works, compared to no mask.

NIH, NIEHS, "Lung Diseases", describes lung diseases.

"Efficacy of a heat exchanger mask in cold exercise-induced asthma" of Beuther D A, Chest 2006 May; 129(5): 1188-93, describes a mask that works as well as the drug albuterol pretreatment.

Rodrigo Athanazio, "Review-Airway disease: similarities and differences between asthma, COPD, and Bronchiectasis", Clinics 2012; 67(11): 1335-1343, 2012, discloses the diseases, risk factors, pathophysiology, symptoms, diagnosis, and treatment of diseases amenable to use with Applicant's invention.

Maria D'Amato, et al, "The impact of cold on the respiratory tract and its consequences to respiratory health", et al. Clinical translation Allergy, (2018) 8.20, discloses the negative effects of cold air in indoor environments such as cars, offices, homes, shopping centers, hotels, nursing homes, hospitals, and the like.

Moreover, when modified to provide heat at specified increased air temperatures, the present invention is useful in therapeutic application. For example, COVID-19 disease, and the subsequent worldwide pandemic, is an exemplary place for use of the Applicant's invention. Wikipedia at "Coronavirus", 2020, describes a more complete exposition of Coronaviruses and COVID-19, including Epidemiology and Symptoms, and incidence of COVID-19. While Coronavirus can encompass several strains of viruses, the most vehement is the SARS-CoV-2 Virus, which causes COVID-19 disease.

Wikipedia "Respiratory Tract" discloses a diagram of respiratory tract, showing upper respiratory tract and a lower respiratory tract. Medline Plus, Feb. 3, 2020 discloses a Diagram of Upper Respiratory tract with an overview.

The New York Times, Pam Belluck, Mar. 26, 2020, "What Does the Coronavirus Do to the Body?", discloses how the virus causing COVID-19 disease, (SARS-CoV-2) causes infection, moves from the upper respiratory tract (i.e., through the nasal cavity, nostril, mouth, throat (pharynx), voice box to the lower respiratory tract, (trachea, primary bronchi and lungs).

WebMD, in "What Does Coronavirus Do to Your Body?" discloses how the virus moves through the person's body from initial infection to the lower respiratory system.

Bloomberg Businessweek, Mar. 8, 2020, in Jason Gale, "There is a Tipping Point Before Coronavirus Kills", discloses how the (SARS-CoV-2) treks to the lower respiratory tract and marks a severe phase progression, from mild or moderate to severe, which can occur quickly".

The virus causing COVID-19 is very sensitive to heat inactivation. See K. H. Chan, "Effects of Temperature and Relative Humidity on the Viability of the SARS Coronavirus", doi,org, Article ID 734690, 2011, which discloses that the virus causing COVID-19 is inactivated at 132.8 Fahrenheit for 15 minutes in vitro. Moreover, Chan discloses that direct application of air, at high temperature and at high relative humidity, has a synergistic effect on inactivation of SARS CoV viability, while, in comparison, lower temperatures and low humidity support prolonged survival of the SARS-CoV-2 virus on contaminated surfaces. Chan also found that the COVID-19 virus is inactivated by exposure to air temperature of 132.8° F. at 80% humidity, but over a prolonged period of 24 hours.

The World Health Organization (WHO), in "Emergencies preparedness, response, first data on stability and resistance of SARS Coronavirus compiled by members of WHO laboratory network" discloses that the virus causing COVID-19 is inactivated at 15 minutes in 1% fetal calf serum, in 15 minutes, at 132.8° F. WHO further discloses that the virus causing COVID-19 cultured in 1% bovine serum is inactivated in excess of 98.6° F. for at least one hour.

Consumer Lab, in "Heat to kill Coronavirus" discloses that heat in moderate to high ranges can be used to inactivate Coronaviruses. This article further cites Chinese studies disclosing inactivation of Coronaviruses at 167° F. within 30 minutes, 60 minutes at 152° F. and 90 minutes at 132° F. The Coronavirus used in these experiments are similar to SARS-CoV-2, but are not the same as the virus causing COVID-19 disease.

The Ford Motor Company, to take advantage of the proven heat sensitivity of SARS-CoV-2 virus causing COVID-19, has reconfigured the climate control system on cars with a software patch, to elevate temperatures to 132.8° F., which they confirmed would kill viral concentrations by in excess of 99% on surfaces and in the air.

See Mark Wilson, in Fast Company, May 29, 2020, "Ford kills COVID-19 with ingenious car heater hack".

Saunas have been used for thousands of years. See Wikipedla at "The Finnish Sauna". The earliest versions date from 7000BC. Millions of people have used them in the intervening years with great safety. The sauna room, which is the sauna, is generally warmed to 176-230° F., op cit. The sauna room exposes the entire body to the heat.

"The Physics Factbook", edited by Glen Elert, discloses different ranges of temperatures of Sauna units, at 176-212° F., 150-194° F., 170-180° F., and 160° F.

"High Heat May Kill the Coronavirus", presented by MERCOLA'S, PEAK FITNESS, discloses a video attached disclosing 10 men and 7 women were exposed to a sauna at 176° F. for 7 consecutive days, twice a day, uneventfully. Disclosed are the many health benefits of the sauna, including immune stimulatory effects such as generation of Heat Shock Proteins and increase in autophagy. Disclosed is the ideal temperature of a sauna at 156-212° F. for 15-30 minutes, 2-4 times a week.

"Can Sauna Kill Coronavirus? We know about Sauna and Coronavirus" Sauna Health, which disclosed that the temperature reached in sauna can kill coronaviruses on the skin.

Moreover, further disclosed in "1" "Steam Baths, Infrared Saunas, and Dry Saunas will not kill a Coronavirus that has reached an infected person's lungs" "Because of a very efficient thermal regulation system, the temperature in your lungs will stay around 37° C. (normal body temperature) no matter how long you stay in the sauna." "Once the virus reaches the lungs it is safe from event the most extreme Finnish Sauna." Infectious disease expert Michael Osterholm discloses in an interview cited here that ostensibly, a sauna is not a cure for COVID-19.

"Emma, in "Ideal Sauna Temperatures: How Hot Is Your Sauna?", 2020 discloses the Finnish sauna temperature is typically 160-194° F. for 30 to 45 minutes. It also discloses that "the American standard implies temperatures from 160 to 194° F., but in many European countries, allowed temperatures are in the range of 160 to 220° F." and, "However, the Finnish Sauna Society recommends that the temperature in the sauna should be from 176 to 194° F. (80-90° C.) with the ultimate maximum of 212° F. (100° C.").

"Thermoregulation" Heathline, discloses that sweat cools human skin as it evaporates, and that the hypothalamus sends signals to various organs and systems in the body.

The skin's immense blood supply helps regulate temperature: i.e., dilated vessels allow for heat loss, while constricted vessels retain heat. The skin regulates body temperature with its blood supply, elevated by temperatures, which are expelled through sweat from the skin with its large surface area. Humidity affects thermoregulation by limiting sweat evaporation and thus heat loss.

Without being limited, held or bound, this is the critical inventive step of the invention. For example, the sauna will not raise the temperature of lung tissue very much, as it is analogous to pouring water into a bucket with no bottom. In the sauna, the entire skin is exposed to heat, opening the pores to expel sweat and heat derived from the enormous blood supply trafficking throughout the body and skin. However, in contrast, the Applicant's invention isolates the respiratory system from the rest of the body and skin so that the respiratory and heated lung tissue generated through the face mask, will disperse/exit more slowly, allowing an elevated tissue temperature in the lung. Instead of having a bucket with no bottom, now there is a bucket with holes in the bottom to drain water out more slowly, allowing a higher lung tissue temperature.

Moreover, "National Cancer Institute" in Hyperthermia in Cancer Treatment" discloses: "Hyperthermia (also called thermal therapy or thermotherapy) is a type of cancer treatment in which body tissue is exposed to high temperatures (up to 113° F.). Research has shown that high temperatures can damage and kill cancer cells, usually with minimal injury to normal tissues (1). By killing cancer cells and damaging proteins and structures within cells (2), hyperthermia may shrink tumors."

This is the "holy grail" of cancer medicine that is most earnestly pursued or sought after. Despite many decades of research, exploitable differences between normal cells and cancer cells remain elusive. Very few, if any, differences exist in tumor and normal cell antigens for targeting. The massive difference in the uptake of glucose by tumor cells against normal cells is one. This resulted in the well-known Positive Emission Tomography (PET Scan). Drugs are currently being designed to support this major exploitable difference in glucose uptake. The differential in sensitivity to heat is another holy grail of cancer medicine, which the Applicant utilizes to treat tumors and dysplasia in the lung.

Cleveland Clinic, Oct. 18, 2018 discloses "Hyperthermia: Why Heat Can Make Cancer Treatments More Potent". They use the application of heat at 109-110° F. with radiation and chemotherapy.

Cystic Fibrosis Foundation discloses in "Infections", that infections in the lung from viruses, fungi, and bacteria are a common problem. The mucous in the lung is an ideal habitat for these pathogens.

Therefore, the Applicant's invention will produce heat shock proteins, and other immunostimulatory molecules, as the invention turns the lung into a bioreactor to produce these agents.

The prior art is non-specific, hitting the entire body, in hitting the respiratory system, and thus is unworkable.

Moreover, Katsarelias, et al, in "The Effect of Temperature and perfusion time on Response, Toxicity and Survival in Patients with In-transit Melanoma Metasteses Treated with Isolated Limb Perfusion", Ann Surg Oncol: 2018; 25(7): 1836-1842, May 15, 2018, discloses a well-established technique to administer "a very high dose" of chemotherapy, at elevated temperature, to isolated tumor sites without causing overwhelming systemic damage.

Also, the Cleveland Clinic, in "Hyperthermia: Why Heat Can Make Cancer Treatment More Potent—Combing heat with chemo or radiation can shrink tumors" Cleveland Clinic Cancer Care website, Oct. 18, 2018, states that heat can be combined with chemotherapy or radiation therapy to reduce or destroy cancer tumor cells.

Additionally, NIH National Cancer Institute, in "Hyperthermia in Cancer Treatment", Aug. 31, 2011, disclosed that hyperthermia cats in combination with chemotherapy and/or radiation can damage cancer cells and enhance the anti-tumor effects of chemotherapy and/or radiation."

OBJECTS OF THE INVENTION

It is therefore an object of the present invention to provide a concentrated heat source to a face mask for destroying pathogens, such as SARS-CoV-2 virus, and other pathogens and for treating lung diseases with high temperature air, (specifically targeting the sites of infection, which causes morbidity and mortality) with relative high humidity.

It is yet another object to provide a heat source, such as a heat gun, to a face mask, such as a Continuous Positive Air Pressure (CPAP) machine face mask for treating lung diseases, such as COVID-19 disease, and other lung diseases with high temperature air with relative high humidity.

It is yet another object to augment cytotoxic chemotherapy and immunology treatments with higher air temperature.

Other objects of the invention will become apparent from the following description of the present invention.

It is also an object of the invention to provide a low-cost apparatus which is battery powered, or gasoline or diesel generator powered, and portable, so that poor people in less developed areas of Africa and the like, with a poor negligible medical infrastructure, can have access to this life saving invention.

It is also an object of the invention to treat up to 20 or more COVID-19 patients at one time off of one single heat gun. All that is required is an individual CPAP mask for each patient, connected by hoses connected to a manifold for multiple, simultaneous deliveries of heated air, at human tolerable temperatures and pressures.

SUMMARY OF THE INVENTION

In keeping with these objects and others which may become apparent, in a preferred embodiment the present invention provides heat source for a heat mask to treat COVID-19 viral disease in a person, as supported by the aforementioned references disclosed herein. Applicant's combination of a concentrated heat source, such as an industrial heat gun and a heat mask in effect isolates and treats the upper and lower respiratory tracts with heated air, at predetermined therapeutic thresholds of both temperature and exposure time duration, to the exact respiratory system sites of SARS-CoV-2 infection, while sparing exposure to the rest of the body.

Applicant's embodiment is a high temperature heat source connected by a heat resistant conduit to a face mask for treating COVID-19, and other bacterial and viral infections of the upper and lower respiratory tracts, and infection of these same tracts by other pathogens.

Applicant proposes a method of destroying a virus causing COVID-19 disease, (SARS-CoV-2) within the respiratory system of a person, comprising the steps of:

a) placing a CPAP mask on the face of the person, the mask comprising a housing mask covering the nose and mouth of the person;

b) connecting a heated air source to deliver air through a hose to the CPAP mask; and c) heating the air to a temperature sufficiently high to destroy the selected pathogen in person's respiratory system.

To accomplish the aforementioned method, Applicant's invention includes a therapeutic face mask combination of a heat source, such as a heat gun, connected by a flexible tubing conduit to a face mask for persons afflicted with the virus causing COVID-19 disease, (SARS-CoV-2) including:

1) a heat source that provides adjustable heated and therapeutically tolerable pressurized air for inhalation;

2) a face mask worn over and covering the nose and mouth of the person; and, 3) a flexible conduit providing the heated and pressurized air to the person through the face mask, wherein the heated and pressurized air is breathed in through the face mask during respiratory breathing of the person.

The aforementioned heat source, such as, but not limited to, a heat gun, preferably has a temperature gauge monitoring temperature for adjustment of the amount of heat generating current to raise the heat to predetermined temperature, to treat the person afflicted with the virus causing COVID-19 disease, (SARS-CoV-2). The air for inhalation by the person is heated in the heat source, by an electrically resistive material contacting a powered airflow from the heat source. The temperature of the resistive material and of the heated air generated are regulated/adjusted by increasing or decreasing the current output settings on the power source, so that heated air is produced at a first predetermined temperature capable of inactivating the virus causing COVID-19 disease, (SARS-CoV-2) for a predetermined time.

As noted in the K. H. Chan reference, op cit, the virus causing COVID-19 is very sensitive to heat inactivation. See K. H. Chan, which discloses that the virus causing COVID-19 is inactivated at 132.8° F. for 15 minutes in vitro. Moreover, Chan discloses that direct application of air, at high temperature and at high relative humidity, has a synergistic effect on inactivation of SARS CoV viability, while, in comparison, lower temperatures and low humidity support prolonged survival of the SARS-CoV-2 Virus on contaminated surfaces. Chan also found that the COVID-19 virus is inactivated by exposure to air temperature of 132.8° F. at 80% humidity, but over a prolonged period of twenty-four hours.

The World Health Organization, (WHO) in "Emergencies preparedness, response, first data on stability and resistance of SARS Coronavirus compiled by members of WHO laboratory network" op cit, disclosed that the virus causing COVID-19 is inactivated at 15 minutes in 1% fetal calf serum, in 15 minutes, at 132.8° F. WHO further discloses that the virus causing COVID-19 cultured in 1% bovine serum is inactivated in excess of 98.6° F. for at least one hour.

Therefore the present invention is configured to deploy heat in a range of from about 80 F to about 275° F., preferably in a range exceeding the 132.8° F. threshold of inactivating SARS CoV-2 virus in vitro at temperatures that mimic Sauna temperatures, directly from a heat source, such as, for example, a programmable heat gun with shutoff safety features, with air temperatures of from about 140° F. to 220° F., that are provided at human tolerable air pressures that mimic air pressures in a CPAP machine, for a medically predetermined period of time, so that the heated air contacts and inactivates the SARS CoV-2 virus accumulated in the upper respiratory epithelial cells of the person suffering form COVID-19 disease. Exposure of the epithelial cells in the throat, epiglottis, trachea, and bronchial tubes is thought to inactivate the SARS-CoV-2 virus in vivo.

Preferably, in the therapeutic face mask apparatus, the aforementioned heat source is a heat gun, having temperature and air pressure controls capable of maintaining the heated air above a minimal effective amount to inactivate a pathogen, such as the SARS CoV-2 virus, and below a second predetermined upper limit threshold temperature and air pressure for safe inhalation.

For safety, preferably, the heat gun includes a switch, wherein if the second predetermined threshold temperature and air pressure for safe inhalation is exceeded, the heat gun will not operate and a visual display with display “OFF”.

Also for safety, the heat gun optionally includes a lock, such as for example, a magnet lock, used for locking a predetermined temperature range and the range of air pressure between the first predetermined temperature and air pressure capable of inactivating the virus causing COVID-19 disease (SARS-CoV-2) and the second predetermined upper limit threshold temperature and air pressure for safe human inhalation.

Further preferably, and optionally, the heat gun includes a keyboard capable of programming the first and second predetermined temperatures and air pressures, that are tolerable to humans.

While the power source for the heat gun is AC power, optionally the power source can alternatively be a low voltage DC power source, such as a battery, or the power source can be AC power transformed to a low voltage DC power source.

Besides treating SARS-CoV-2 induced COVID-19 disease, there is also provided a method of treating selected pathogens and lung diseases, selected from the group consisting of bacteria, viruses, fungi, mycoplasma, asthma, mesothelloma, lung cancer, dysplasia, chronic obstructive pulmonary disease (COPD), emphysema, chronic bronchitis, pulmonary fibrosis, cystic fibrosis, pneumonia, heart disease and other cancers which metastasize to the lung or respiratory system.

Preferably, the heat gun heats air to a sufficiently high temperature is between about at least 80° F. and about 275° F., optionally, in which the sufficiently high temperature is at least 132.8° F. up to about 230° F. Also, optionally, the humidity is preferably about 90 to 95%, which is maintained by human respiration in the throat of a person being treated.

In order to keep the pressure of the heated air at a tolerable level compatible with human respiration, the air pressure of the heated air is compatible with typical air pressure flows in a Continuous Positive Air Pressure (CPAP) machine. Most CPAP machines pump air in the range from 6 to 15 cm/H20 (centimeters of water pressure), such as, for example, an air flow is set at 8 cm/H2O.

To convert that to air pressure measured in millimeters of mercury (Hg), one divides the cm/H2O amount by a factor of 1.36. Therefore, a CPAP air flow pressure of 8 cm/H2O is divided by a factor of 1.36, wherein 8/1.36=5.88 Hg. Stated in psi (pounds per square inch), an 8 cm/H2O=5.88 Hg, or 2.88 psi.

Even at the upper limit of 15, the air pressure being pumped from a CPAP machine into the person is only 11 Hg, or 5.4 psi.

Since typical heat guns are not designed to expel the heated air at such human tolerable air pressures that are regularly set in CPAP machines, there is a needed determination to make sure that the heated air, which is heated at a predetermined temperature comparable to inactivate the SARS Cov-2 virus in the epithelial cells of the human respiratory system, for example, or at sauna levels of 150 F or above, is pumped into through a CPAP-type tube (rated for high temperatures) and into the person’s CPAP-type face mask at air pressure of no more than 11 Hg, or 5.4 psi at the upper level of human respiratory tolerance, or preferably a lower amount, such as for example, at 5.88 Hg or 2.88 psi.

For safe inhalation at human respiratory rates, the volume of air must be controlled down from the high rates capable of being expelled by a heat gun in industrial applications, down to an acceptable level tolerable by human respiration. For example, tidal volume (symbol VT or TV) is the typical human lung volume, representing the normal volume of air displaced between normal inhalation and exhalation when extra effort is not applied. In a healthy, young human adult, the tidal volume is approximately 500 mL per inspiration or 7 mL/kg of body mass. Furthermore, a normal minute volume, while resting, is about 5-8 liters per minute in humans. Minute volume generally decreases when at rest and increases with exercise. For example, during light activities, minute volume may be around 12 liters. Since heat guns are capable of producing heated air at about 190 liters per minute, the air volume can be titrated down to 5-8 liters per minute, or 12 liters per minute, or 50 liters per minute, whichever is best for the person being treated.

In the present invention, the heat gun must have the capability of providing heated air in the range of 80° F. to 275° F., preferably at sauna heat temperature levels of about 150 to 230° F., and at air pressure levels of no more than about 5.4 psi for human respiratory tolerance. While any heat gun which is capable of the aforementioned temperature and air pressure range limitations, non-limiting examples of such heat guns include the Master Pro Heat Gun models 1400 and 1500.

In the Master heat gun model 1400, which operates at 120/230 V AC, outgoing air temperatures can be as low as 130° F., extending up to 1000° F. The Master heat gun model has a finger-operable ON/OFF switch on a trigger position of the handle, which has three setting depending upon selected movement of the switch. In a “HEAT” position, the top of the switch is depressed inward. To achieve a “COOL” position, the switch is set so that the top and bottom portions are equally extended. To turn the switch off, the bottom of the switch is completely pushed inward.

For use in provided heated air through a heat resistant flexible hose to a CPAP type face mask covering the nose and mouth of the person, the Master Pro Heat gun model 1400 can also be set at a human tolerable upper limit, such as for example 200F or even 300° F., if medically appropriate, at air flow volumes of as little as 4 CFM (cubic feet per minute). The rear of the heat gun handle has a pair of turnable knobs, where the left knob is twisted and turned to adjust the airflow up or down to predetermined human tolerable levels, which are displayed in an LCD screen above or adjacent to the knobs. To adjust the temperature of the emitted air, the right knob is twisted and turned to raise or lower the designated heat of the air flow output. A set temperature is displayed for several seconds, until the actual output air temperature is displayed on the LCD screen.

A further safety feature in the Master Pro Heat gun model 1400 is that adjacent to the two knobs there is provided a locking lever or key, typically but not necessarily magnetic, that is pushed or moved to set and lock the output air temperature and pressure. The settings inputted by the two knobs cannot be changed if the LCD indicates a “Lock” icon, due to the manipulation of the locking lever or key. The locking lever or key can alternatively be used for converting the temperature from Fahrenheit units to Celsius.

Alternatively, the Master heat gun model 1500, also operates at 120/230 V AC, outgoing air temperatures can be as low as 130° F., extending up to 1000° F. The Master heat gun model 1500 also has a finger-operable ON/OFF switch on a trigger position of the handle, which has three setting depending upon selected movement of the switch. In a "HEAT" position, the top of the switch is depressed inward. To achieve a "COOL" position, the switch is set so that the top and bottom portions are equally extended. To turn the switch off, the bottom of the switch is completely pushed inward.

For use in provided heated air through a heat resistant flexible hose to a CPAP type face mask covering the nose and mouth of the person, the Master Pro Heat gun model 1500 can also be set at a human tolerable upper limit, such as for example 200F or even 300 F, if medically appropriate, at air flow volumes of as little as 4 CFM (cubic feet per minute). The rear of the heat gun handle also has an LCD screen, but adjacent to, or below, the LCD screen there is provided an array of programmable settings with keypad up/down arrow keys, where the left up and down arrow keys are manipulated to adjust air pressure and the right up and down arrow keys are manipulated to adjust the temperature up or down to predetermined human tolerable levels, which are displayed in an LCD screen above or adjacent to the key pad. In the middle between the left and right-side arrow keys are two other keys, where the upper key has a "P" inscribed thereon, for program the desired inputted air pressure and temperature outputs. The lower middle key is used to change the output levels from Fahrenheit to Celsius, or vice versa.

A further safety feature in the Master Pro Heat gun model 1500 is the programmable keys can be used to set and lock the output air temperature and pressure. The settings inputted by the two knobs cannot be changed if locked by the programmable keys.

While other heat guns with the aforementioned locking capabilities can be used, another example is the Steinel pistol grip heat gun model HG 2520 E which can produce temperatures in the range of from as low as 120° F. up to 1300° F. (50 to 700° C.), which has pressures as low as from 2 to 13 CFM, and programmable safety override functions. Additionally, the Seekone Heat Gun 1800 W has a dial with variable temperature controls.

Another useful heat gun for providing the elevated heat source is the Wagner 0503049 HT4500 Heat Gun, which has fifty-five temperature choices by button. The temperature of the outgoing air at the nozzle tip of the Wagner HT 4500 heat gun can be as low as 120° F. minimum. As the heated air travels through the flexible heat resistant hose, the temperature of the air is reduced at the beginning of the CPAP mask to about 100° F. The Wagner HT 4500 heat gun has an LCD screen at the back of the gun, with a pair of touch responsive keypad buttons for increasing or decreasing temperature, and another set of touch responsive keypad buttons for increasing or decreasing output air pressure.

In a hospital setting, the heat gun can be installed on a collapsible folding cart, with an AC wall outlet or, optionally, to a Honda generator on the cart for full ambulatory use (when in ventilated conditions to eliminate carbon monoxide), which lasts over eight at ¼ power. It can last over three hours at full power, and by dividing the pressurized heated air, can treat at least ten people with one machine. For example, the conversion of CFM to liters per minute is 28.32; thus, a heat gun at 120° F. heat at 3.5 CFM times the factor of 28.32=99.12 liters per minute. Since a human takes 5-8 liters at rest, therefore the present invention can bleed off 99.12 minus 8=91.12 liters per minute, for treating about ten persons people simultaneously.

While the aforementioned heat guns require 120V AC power to operate other cordless heat guns with rechargeable batteries can also be utilized to provide controlled hear and air pressure suitable for human respiration, with air pressure reduction controls, so that the pumped air is limited to the human tolerable air pressures of about no more than about 5.4 psi. An example of a cordless heat gun that can run up to 42 minutes between recharging the battery is the DeWalt 20V Max Cordless Heat Gun. Another cordless heat gun is the Ryobi cordless 18V heat gun has a concentrated heated air flow typically used for electronic board repair applications such as shrinking shrink tubing for insulating cable ends, or at high temperature removing defective modules by melting solder at the contact tabs. It is powered by a 3 Ah 18v battery that weighs 1.72 pounds (and stores 54 Wh worth of energy).

For further safety control, anti-microbial or stainless-steel hygienic ball valves can be deployed in the flexible heat resistant tubing, between the heat gun heat source and the CPAP-type face mask. A first ball valve may be deployed as a "T" configuration, such as an Eldon James Antimicrobial high density polyethylene (HDPE) threaded tee, in line with the heat gun output nozzle and the hose of a flexible polymer tubing, such as, TYGON 3350 or TYGON 54297. The hygienic ball valve, which is preferably is one of ¾ full port SS 2-pc. ball valves, is connected at the T with a hose coming off of it, functioning as a pressure bleed valve. A second hygienic ball valve is a resister valve deployed near the mask, which, as a restrictor valve, restricts air from the gun traveling into the mask if it exceeds medically acceptable values. Manipulation of these two valves achieves the desired airflow and heated temperature of the air being delivered from the heat gun to the person, through the CPAP-type mask. An anemometer is used to calculate the cubic feet per minute (CFM) volume or mass air flow at the interface of the flexible hose and the CPAP type mask worn by the patient being treated.

Other optional safety controls include air pressure controllers, to keep the heated air at those lower levels of pumped air pressure, compatible to what are used conventionally in CPAP machines, so that the incoming heated air flow is also limited to "human tolerable air pressure", which typically may be no more than about at 15 cm/H2O, or 11 Hg, or 5.4 psi, or within the CPAP acceptable range of air pressure of 6 to 15 cm/H20, or 4.4 Hg to 11 Hg, or 2.16 psi to 5.4 psi.

For those low human tolerable air pressure flows, optionally there may be provided a microprocessor-controlled air pressure distributor associated with the heat gun, so that the psi of the outgoing air pressure can be maintained at those low human tolerable air pressures, regardless of the heat of the air.

In general, since the device is a medical device, optimally the heat guns have air temperature and air pressure controls, such as thermostats for temperature control, with automatic shutoff features and interlock. For example, the Master Pro Heat gun has a minimal CFM of 4 and a safety interlock built-in for temperature and air flow stopping. Converted to liters=0.28 Liters per minute, this is below the air flow of a human at rest with normal activities, which is about 5-8 liters per minute.

In connection therewith, while the heat guns may have finger operable keys for controlling air temperature and air pressure, optionally these person operable controls and shutoffs may also have a simple AC wall outlet plug-in adapter that acts as a fail-safe automatic shutoff and interlock preventing any heat output above a threshold maximum and preventing any air pressure above a threshold maximum, such as tolerated in a CPAP machine, to prevent accidental increases of temperatures and air pressures above what is tolerable in human respiration.

Since a heat gun is a powerful device plugged into potentially lethal voltage and can deliver powerful airflow and temperatures to 1000° F., Applicant has tested temperatures at the tip of the heated air output, at a distance of one inch out therefrom, of the heat gun when on full heat, in replicate six+times. When the heat gun claims to emit heated air at 1200° F., Applicant measured the actual heated air from the heat gun to be about 487° F. Therefore, the listed manufacturing of heat guns' base temperature on the red-hot nozzle tip at a distance of about two inches from the tip of the heat gun is widely exaggerated. However, it may be desirable in certain environments to use a safety interlock AC outlet plug-in adapter, to separately monitor the temperature and pressure delivered to a patient and to shut down the system in case either the pressure or temperature in the patient hose exceed predetermined safety limits of heated air and pressure, tolerable in human respiration.

In general, in case of shut down, manual intervention (physically pressing the start button) is often required. Since the safety interlock plug-in adapter is plugged into the wall outlet and the heat gun is plugged into the adapter (like plugging three prong plugs into two prong wall outlet adapters), the heat gun need not be modified, but an extra degree of safety would be gained by changing the plug or line cord and plug of the heat gun to one with a keyed plug that no longer fits a wall plug. A mating outlet on the safety plug-in adapter would fit the keyed plug of the heat gun.

Such a simple interlock adapter that is plugged into an AC outlet between the AC outlet and the AC compatible plug of the heat gun typically includes an AC relay, with normally open single pole contacts. An AC coil and related contacts make up a simple relay, which has separate ON and OFF momentary switches. One switch has normally open contacts and the other switch is in the relay latching circuit and it has normally closed contacts. A thermal sensor switch with normally closed contacts is selected from a factory list of available temperatures. The maximum temperature selected must be above the range of operating temperatures. A normally closed pressure sensing switch interfaces with the airflow to sense a pressure beyond operating region that is close to being a safety hazard. A fuse can complete the circuit.

The aforementioned simple interlock plug-in adapter is a fail-safe shutoff to completely shut the heat gun down, if the heat gun itself has a malfunction in its operation or use.

The aforementioned heat guns provide heated air to persons afflicted with the primary cause of mortality and morbidity in SARS-CoV-2 infections, also known as COVID-19 disease, which is caused by the accumulation of the virus in the lung. The SARS-CoV-2 virus is intracellular here, within surfactant producing lung cells. Suffice it to say the SARS-Co-V-2 virus is in a 100% wet environment within the epithelial cells of the patient's respiratory system. Applicants heat hits these cells containing the virus with heat.

In contrast to a sauna room chamber, which achieves a high in vivo temperature of the entire body of a person, but lacks specificity for heating on specified exact identifiable sites of infection, in the present invention, the delivered heated air is site-specific in the epithelial cells of the patient's respiratory system. Specificity is the sought-after goal of medicine, i.e. the earnestly pursued proverbial "holy grail", namely, to target only the exact sites of infection, while sparing the rest of the body.

The Applicant's invention achieves specificity for the bulk of infection of COVID-19 disease causing SARS-CoV-2 virus in the upper and lower respiratory tracts of a human patient. The primary cause of mortality and morbidity in COVID-19 disease caused by the SARS-CoV-2 virus in the lung. The SARS-CoV-2 virus is intracellular here, within surfactant producing lung cells. Suffice it to say the virus is in a 100% wet environment within the cell. The high temperature heat of the therapeutic heated mask of the present invention hits the upper and lower respiratory epithelial tissue cells containing the SARS-CoV-2 virus with heat.

Research has disclosed the non-detrimental effects of increased heat on animals. David A. Rickaby, et al, "Tolerance of the isolated perfused lung to hyperthermia", J Thorac Cardiovasc Surg, 1991; 101:732-9, discloses tests on 23 mongrel dogs with isolated left lower lobes, which shows, "Thus on the timeframe consistent with in vivo perfusion therapy the normal lung appears to tolerate a fairly severe hyperthermia." This temperature is both viricidal, and tumoricidal, when delivered at 113° F.

Then it follows, since these dog lungs tolerated 113° F. with no toxicity, then 113° F. is not the upper limit of temperature that the lung will take, which is very advantageous for the Applicant's invention. This conforms to NCI, op cit. disclosing that tumor cells are killed or damaged at 113 F, while sparing normal cells. The higher the temperature, the better, without toxicity to the patient being treated.

The present invention of Applicant also in effect isolates and treats the upper and lower respiratory tracts, the exact sites of COVID-19 infection, while sparing exposure to the rest of the body.

Duration of exposure to a COVID-19 patient depends on the clinical judgment of the attending medical team. COVID-19 is a nasty disease with multi focal disease in both lungs. For lower temperatures, up to about 105° F., 24 hours a day, 7 days a week. Higher Temperatures above 105 depends on the judgment of the medical team. Each patient will be evaluated by the medical team for performance status and lung parameters, to determine appropriate treatment. Typical exposures of the higher temperatures are about 10-60 minutes, up to 24 hours in controlled observed situations, which are repeated at the medical team's evaluation and judgment.

Temperature of treated air can be provided from a heat gun through a heat resistant flexible tube to the face mask, at a range of about 80 to about 300° F. A more preferred temperature is about 125-212° F. It is noted that the 212° F. air temperature conforms to the Finnish sauna data, as per Wikipedia, Finnish sauna history, which is. believed to have been used for 7,000 years by millions of people. Another preferred temperature range is about 156° F. to about 212° F., conforming to the video of Mercola, op cit, and, in conformity with existing sauna usage, preferably about 156-212° F. Heated air temperatures employed in the present invention mimic the tried and true proven air temperatures of Finnish saunas, which have been experienced safely by millions of people for centuries in Scandinavia.

The heated air of the present invention may not hit the lower respiratory system's lungs with the same degree of efficacy as hitting the upper respiratory tract, as the lower respiratory tract infection is intracellular, but it is beneficial to block progression of the COVID-19 virus from traveling from the upper respiratory tract to the lower respiratory tract. To inactivate the SARS-CoV-2 virus significantly, in mild to moderate COVID-19 viral disease, the heated air of the present invention contacts and renders viruses in the upper respiratory tract non-infective and inactivated.

The respiratory heated air, delivered from a heat gun through a flexible heat resistant tube to a therapeutic face mask, which is configured for inactivating pathogenic viruses in a wearer's upper and lower respiratory system, contacts resistant viruses, such as the Coronavirus SARS-CoV-2 in the wearer's upper respiratory sinuses, throat, trachea, and upper bronchial tubes and lower respiratory bronchial tubes and lung alveoli; and also promotes the wearer's immunostimulatory response to the respective pathogenic virus.

The primary cause of mortality and morbidity in COVID-19 disease caused by the COVID-19 virus is the lung. The SARS-CoV-2 virus is intracellular here, within surfactant producing lung cells. Suffice it to say the virus is in a 100% wet environment within the cell. The high temperature heat of the therapeutic heated mask of the present invention hits the upper and lower respiratory tissue cells containing the virus with heat.

Therefore, in the preferred embodiments, for treating COVID-19 virus and other pathogens and lung diseases, the therapeutic combination heat gun, flexible tube and face mask, which is adapted for covering the nose and mouth of a person. The face mask is connected by a conduit, such as a flexible tubing to a heat gun for heating incoming air and providing the incoming air at a safe air pressure for inhalation and exhalation.

A front entry of heat gun is adapted for delivery of the heated incoming air to mix with the high relative humidity of the exhaled air of the person's upper respiratory system, nose and mouth. Preferably, the flexible tube has manipulatable hygienic anti-microbial plastic or stainless-steel ball valves, and a bleeder, for initially safely setting a safe flow of heated air to a patient.

Heat is generated through the electric resistive conductive heating elements of the heat gun by a source of electricity, whereby the air passing through the heat gun is heated to a sufficiently high temperature to destroy selected pathogens, such as SARS-CoV-2 virus, and to treat other diseases within the respiratory system of the person.

In preferred embodiments, the heat gun may be portable and wearable upon a person's belt, so that an ambulatory person can use the high temperature therapeutic heat through a CPAP type mask, which is attached by a flexible tube connected to the heat gun capable of providing heated air in inhalation, at predetermined high levels of heated air, in a humidified environment, at a safe air pressure, to maintain intact the upper respiratory system infected by a resistant virus, such as, for example, the SARS-CoV-2 virus, at a further predetermined heated temperature level, to deactivate the resistant virus and promote an immunostimulatory response in the patient.

The preferred embodiment can also be used in a hospitalization setting, where a bedridden person can use the high temperature air produced by a heat gun, in conjunction with a CPAP type mask attached by a flexible tube connected to the heat gun, which is capable of providing heated air in patient respiratory inhalation at predetermined high levels of heated air, in a humidified relatively low air pressure environment, to maintain the upper respiratory system infected by a resistant virus, such as, for example, the SARS-CoV-2 virus, at a further predetermined level, to deactivate the resistant virus and promote an immunostimulatory response in the patient.

While temperatures may vary, for treating SARS-CoV-2 virus for a predetermined period of time, the sufficiently high temperature is preferably between about at least 80° F. and about 300° F. or optionally between 130° F. and 230° F. In a preferred optional embodiment, the sufficiently high temperature is at least 132.8° F. and the high relative humidity of about 95%, when administered for at least 15 minutes. Alternatively, the sufficiently high temperature of at least 132.8° F., but with a relative humidity of about 80%, will be needed to be administered for a longer period of time.

The method of treatment includes destroying selected pathogens, such as the SARS-CoV-2 virus, and/or treating lung diseases which are selected from the group consisting of bacteria, viruses, fungi, asthma, mesothelioma, lung cancer, chronic obstructive pulmonary disease (COPD), emphysema, chronic bronchitis, pulmonary fibrosis, cystic fibrosis and pneumonia.

Besides being used for treating SARS-CoV-2 virus, the combination heat gun, connecting tube and face mask may be used for destroying selected other pathogens and lung diseases, which are selected from the group consisting of bacteria, viruses, fungi, asthma, mesothelioma, cancers, lung cancer, chronic obstructive pulmonary disease (COPD), emphysema, chronic bronchitis, pulmonary fibrosis, cystic fibrosis and/or pneumonia, an add-on to cytotoxic chemotherapy and radiation, and immunotherapy.

The method of providing elevated heat at human tolerable temperatures and air pressures optionally further comprises the steps of augmenting cytotoxic chemotherapy or immunotherapy for cancers of the lung, upper and lower respiratory tract and other body parts of a person by supplying said heated air to the person afflicted with the disease, by heating the air to a temperature sufficiently high to augment said cytotoxic chemotherapy or the immunotherapy and causes an immunological upregulation at the sites of the person being treated with the immunotherapy, or by treating cancer by supplying said heated air sufficiently high to treat cancer. A further option is the administration of a supplement to the person, such as at least Vitamin C, as an adjuvant to the treatment method.

BRIEF DESCRIPTION OF THE DRAWINGS

The present invention can best be understood in connection with the accompanying drawings. It is noted that the invention is not limited to the precise embodiments shown in the following drawings, in which:

FIGS. 6, 6A and 6B show an optional real time collar adapter for the heat gun of FIGS. 1, 1A, 2, 3, 4 and 5.

FIG. 7 is a perspective view of an ambulatory adult, with a portable cordless heat gun suspended in a holster and powered by a rechargeable battery.

DETAILED DESCRIPTION OF THE INVENTION

The present invention discloses high temperature, high humidity therapeutic heat masks for treating resistant pathogens, such as SARS-CoV-2 virus, and other lung diseases, in drawing FIGS. 1-7.

Figure 1:
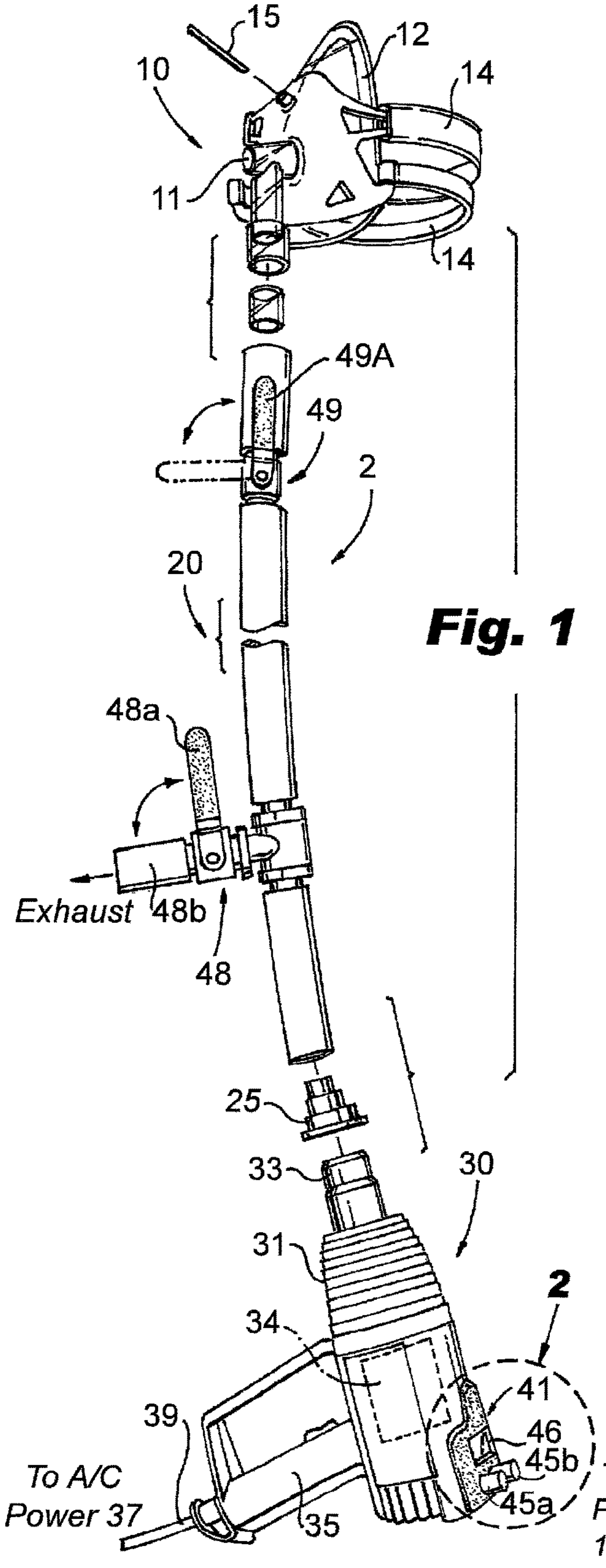
FIG. 1 is a front perspective view of a person wearing a face mask connected by a flexible tube having safety ball valves to a heat source, such as a heat gun.

FIG. 1 shows a first embodiment 2, including a therapeutic combination of a heat source, such as a heat gun 30, connected by a flexible tubing conduit 20 to a face mask 10 for persons afflicted with the virus causing COVID-19 disease, (SARS-CoV-2). The heat source 30 provides adjustable heated air and therapeutically tolerable pressurized air for inhalation by a patient afflicted with COVID-19 disease, caused by the specific Coronavirus known as SARS CoV-2 virus. A face mask 10 includes a rotatable connector 11 attachable at one end to a heat resistant flexible conduit tube 20, similar to that of a CPAP machine. The face mask 10 also has a flexible cushion 12, general triangular shaped, covering the nose at its top end, with tapered flexible, sealed side edges, and a rounded bottom, sealed edge, covering the mouth of the patient, Headgear straps 14 are provided to wrap around the skull of the patient, to maintain the face mask 10 in a secure, non-movable position covering the nose mouth and adjacent face, cheek and chin areas of the patient. The face mask 10 is therefore worn over and covers the nose and mouth of the person. The face mask 10 is preferably made from heat resistive materials throughout, in order to withstand heat in excess of about 200° F. or more, if required.

Optionally, the face mask 10 may have an optional built-in thermometer 15 for a health care provider to visually monitor the temperature within the face mask 10.

Further, optionally, for extra sealing around the circumferential edge of the face mask 10, an extra circumferential cushioned standoff, having the same circumferential edge shape as of the face mask 10, and made of foam or other suitable, pliable, cushioned materials, may provide a further sealing interface for the face mask 10.

The heat resistant flexible conduit tube 20 provides the heated and pressurized air from heat gun 30 to the patient, through the face mask 10, wherein the heated and pressurized air is inhaled and breathed in through the face mask 10, during respiratory breathing of the patient. The aforementioned heat source, such as, but not limited to, a heat gun 30, includes a forward barrel portion 31 with a nozzle 33 at a distal end and a person manipulatable handle 35, preferably trigger shaped, wherein the handle extends below the enclosed mechanical and heat producing components, including an electrical power source, such as an electric motor 34, powered by an AC power source 37 connected by a wire 39 to the 120V AC power source 37 in a wall outlet or from a generator 352 shown in FIG. 5, or a DC rechargeable power source 570, shown in in FIG. 7, such as a lithium ion battery, or an AC source transformed to a DC power source, with a built-in power connector inside the heat gun.

Figure 3:
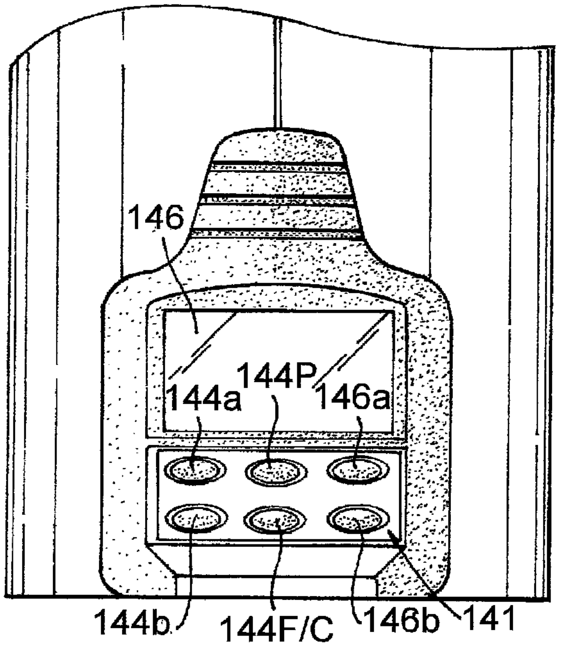
FIG. 3 is a top detail view of the heat gun of FIG. 1A, taken at arrow "3" of FIG. 1A, showing a display with programmable control keys.
Figure 3A:
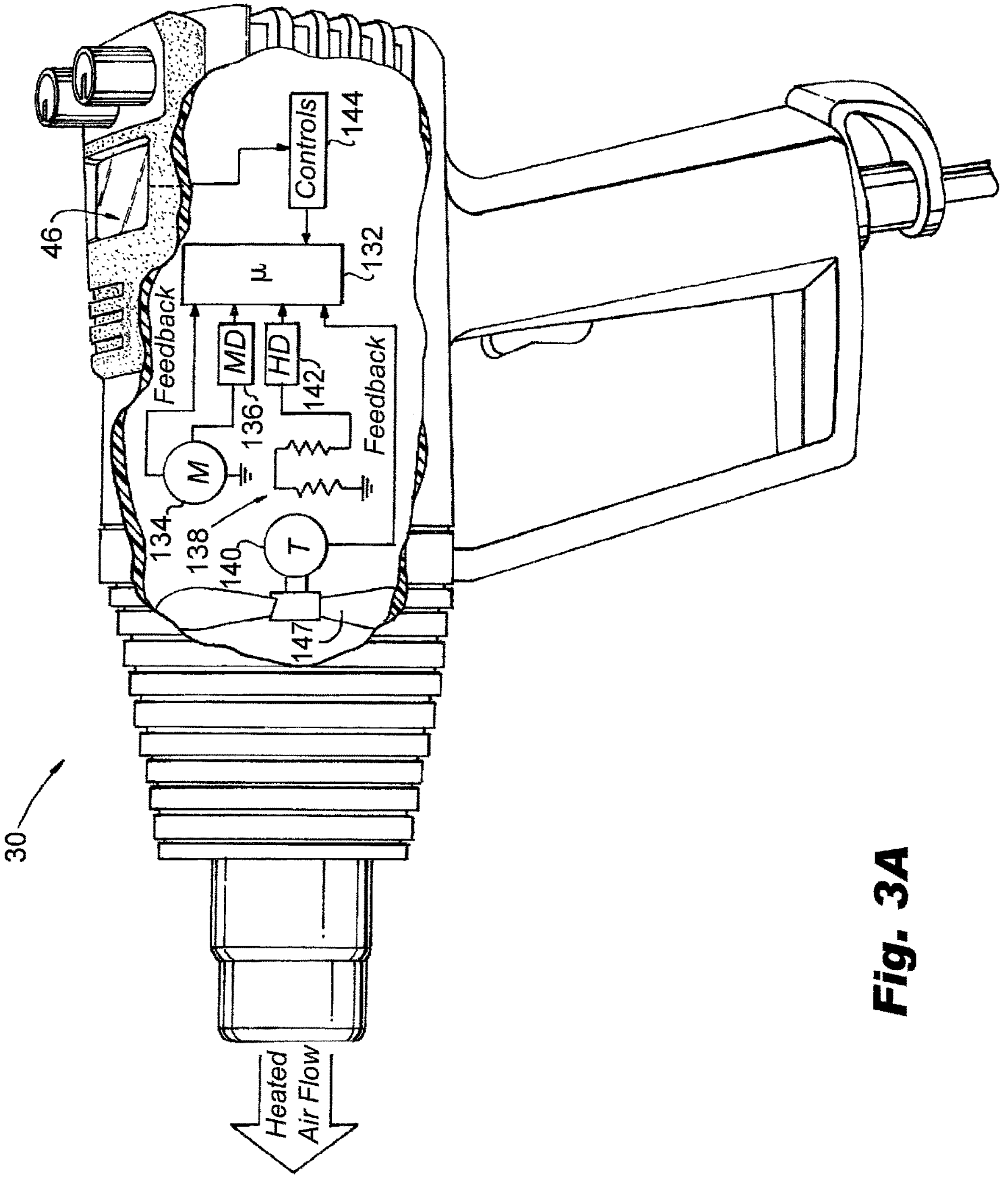
FIG. 3A is a block diagram of the heat gun of FIGS. 2 and 3, shown within the housing of the heat gun of FIG. 1.

The heat gun 30 also includes a resistive component, wherein a fan 147, as shown in FIG. 3A, pulls or blows air past the heating resistive elements 138, and out through the barrel 31 and nozzle 33, into the heat resistant flexible conduit tubing 20 and thereafter through the face mask 10 into the nose, throat and upper respiratory system of the patient, to expose the epithelial cells infected with SARS CoV-2 virus embedded therein to heated air, to inactivate the SARS-CoV-2 virus and to promote an immunostimulatory response in the patient. While fan 147 is shown FIG. 3A in a forward position pulling air therethrough, it can also be positioned to the rear (not shown), behind the resistive elements 138, pushing the air past the resistive elements 138.

The heat gun 30 preferably has a control panel 41 with a visual display screen 46 and controls 45*a*, 45*b* with an internal temperature gauge sensor 140 (shown in FIG. 3A) monitoring temperature for adjustment of the amount of heat generating current to raise the heat to a predetermined temperature, and an air pressure sensor to monitor air pressure at a human tolerable level, mimicking air pressure normally provided to a CPAP person patient having sleep apnea or other treatable respiratory obstructive diseases, to treat the person afflicted with the virus causing COVID-19 disease, (SARS-CoV-2).

As shown in FIG. 3A, the air for inhalation by the patient is heated in the heat source, such as heat gun 30, by an electrically resistive material 138 contacting a powered airflow produced by a fan 147 in the heat source, such as heat gun 30. Depending upon the position of the fan 147, it can pull or push the air past the electrically resistive elements 138 inside the heat gun 30 or 130. The temperature of the resistive elements 138 and of the heated air generated are regulated/adjusted by increasing or decreasing the current output settings on the motor 134, so that heated air is produced at a first predetermined temperature capable of inactivating the virus causing COVID-19 disease, (SARS-CoV-2) for a predetermined time and to promote an immunostimulatory response in the person.

FIG. 1 also shows, for extra safety control, first and second ball valves 48, 49 which are deployed in the flexible heat resistant tubing conduit 20 between the heat gun 30 and the CPAP-type face mask 10. A first ball valve 48, having a manually rotatable handle 48*a*, may be deployed as a "T" configuration, in line with the heat gun output nozzle 33 and the hose 48*a*. The ball valve 48 is connected at the "T" with the hose 48*b* coming off of it, functioning as a pressure bleed valve. A nipple 25 engages within the flexible conduit tubing 20 at one end, which is in-line with the first ball valve 48, and then friction fits over the nozzle 33 of the heat gun 30. A second ball valve 49, also with a manually rotatable handle 49*a*, acts as a resister valve deployed near the mask 10, which restricts air from the heat gun 30 traveling into the mask 10 if it exceeds medically acceptable air pressure values. Manipulation of these two ball valves 48, 49 achieves the desired airflow and heated temperature of the air being delivered to the person through the CPAP-type mask 10.

The heat gun 30 is capable of providing heated air from about 80° F. to 900° F., but in use, is limited to providing heated air to a patient at a minimum temperature of about 130 F, up to a maximum of about 275° F. These temperatures mimic the human tolerable temperatures of from about 130° F. to about 230° F. to which humans are exposed to in heated saunas. These elevated temperatures of heated air contact the epithelial cells inside the throat and upper respiratory system of the patient, to which the SARS CoV-2 virus are attached.

The predetermined temperature, which may vary according to medical needs, initiates inactivation of the SARS Cov-2 virus causing COVID-19 disease, in the infected upper respiratory surfaces of the patient. This threshold temperature can vary from typical about 80° F. to 275° F., preferably at least 132.8° F., up to about 230° F. when combined with a relative humidity, and at a tolerable air pressure mimicking air pressure to a respiratory obstructive/sleep apnea patient using analogously a CPAP machine. While normally CPAP machines treat obstructive respiratory conditions, such as sleep apnea, at a temperature of between 60 and 95° F., depending upon patient comfort, they generally are built to shut off at a 95° F. threshold.

Hence, for the treatment of COVID-19 disease caused by the SARS CoV-2 virus, the temperature should be a minimum of about 130° F., as evidenced in the Chan and WHO in vitro tests results, op cit, listed herein.

This elevated heat treatment which can vary in time from about a minimum of 15 minutes, up to 24 hours, as per medical instructions, is believed to have a synergistic effect on inactivation of the SARS CoV-2 virus, and hopefully a reduction in COVID-19 disease within the respiratory systems of the patient.

Figure 1A:
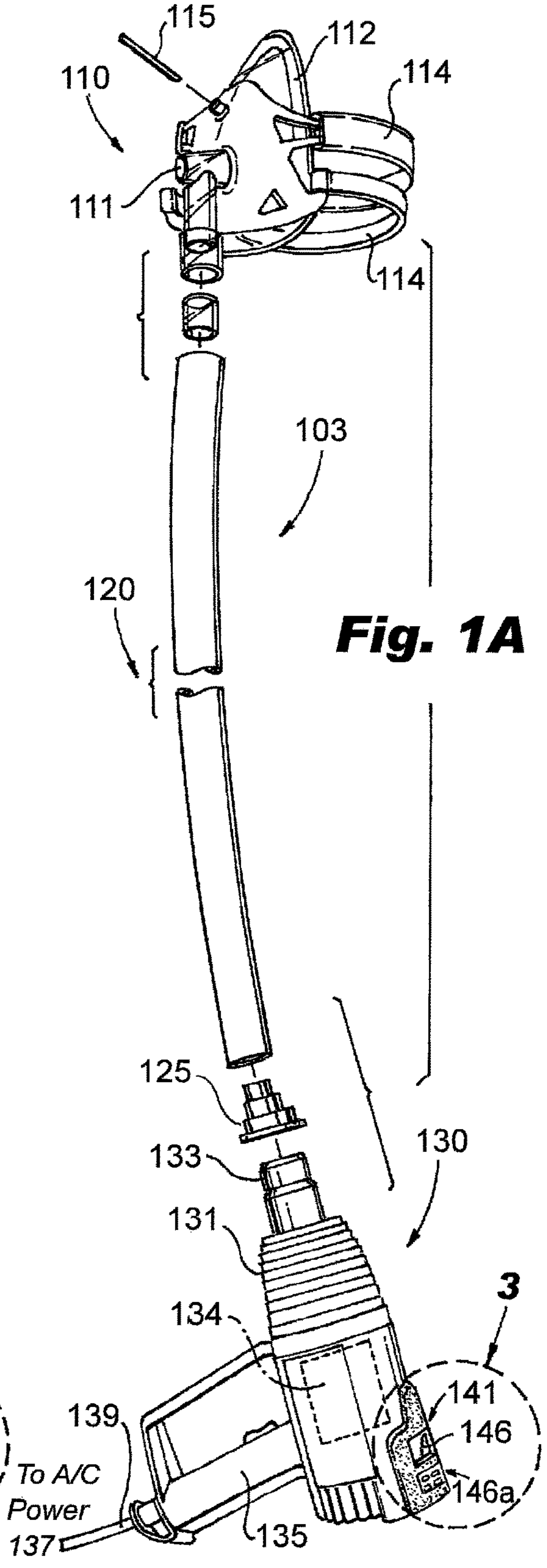
FIG. 1A is a front perspective view of a person wearing a face mask connected by a flexible tube to a heat source, such as a heat gun.

FIG. 1A shows an alternate embodiment 103, including a therapeutic combination of a heat source, such as a heat gun 130, connected by a flexible tubing conduit 120 to a face mask 110 for persons afflicted with the virus causing COVID-19 disease, (SARS-CoV-2). The heat source 130 also provides adjustable heated air and therapeutically tolerable pressurized air for inhalation by a patient afflicted with Covid-19 disease, caused by the specific Coronavirus known as SARS CoV-2 virus. The face mask 110 also includes a rotatable connector 111 attachable at one end to the heat resistant flexible conduit tube 120, similar to that of a CPAP machine. The face mask 110 also has a flexible cushion 112, generally triangular shaped, covering the nose at its top end, with tapered flexible, sealed side edges, and a rounded bottom, sealed edge, covering the mouth of the patient. Headgear straps 114 are provided to wrap around the skull of the patient, to maintain the face mask 110 in a secure, non-movable position covering the nose mouth and adjacent face, cheek and chin areas of the patient. The face mask 110 of FIG. 1A is also therefore worn over, and covers, the nose and mouth of the patient. Optionally, the face mask 110 may have an optional built-in thermometer 115 for a health care provider to visually monitor the temperature within the face mask 110.

The heat resistant flexible conduit tube 120 provides the heated and pressurized air to the patient, through the face mask 110, wherein the heated and pressurized air is breathed in through the face mask during respiratory breathing of the patient. The aforementioned heat source, such as, but not limited to, a heat gun 130, includes a forward barrel portion 131 with a nozzle 133 at a distal end and a person manipulatable handle 135, preferably trigger shaped, wherein the handle 135 extends below the enclosed mechanical and heat producing components, including an electrical power source, such as an electric motor 134, powered by an AC power source 137, connected by a wire 139 to 120V AC power 137 in a wall outlet or from a generator 352 shown in FIG. 5, or a DC rechargeable power source 534, such as a lithium ion battery, as shown in a portable, cordless heat gun 530 of FIG. 7, or an AC source transformed to a DC power source, with a built-in power connector inside the heat gun.

The heat gun of FIG. 1A also includes resistive elements 138, wherein a fan 147 pulls or blows air past the heating resistive elements 138, and out through the barrel 131 and nozzle 133, into the heat resistive flexible conduit tubing 120, and thereafter through the face mask 110 into the nose, throat and upper respiratory system of the patient, to expose the epithelial cells infected with SARS CoV-2 virus embedded therein, for inactivation of the SARS-CoV-2 virus and to promote an immunostimulatory response in the person.

The heat gun 130 of FIG. 1A also preferably has a control panel 141 with a visual display screen 146 and controls 144*a*, 144*b*, 146*a*, 146*b*, with an interior temperature sensor 140 (shown in FIG. 3A) monitoring temperature for adjustment of the amount of heat generating current, to raise the heat to a predetermined temperature, and an air pressure gauge to monitor air pressure at a human tolerable level mimicking air pressure normally provided to a CPAP person patient having sleep apnea or other treatable respiratory obstructive diseases, to treat the person afflicted with the virus causing COVID-19 disease, (SARS-CoV-2). The air for inhalation by the patient is heated in the heat source, such as heat gun 130, by electrically resistive elements 138 contacting a powered airflow produced by a fan 147 in the heat gun 130. The temperature of the resistive elements 138 and of the heated air generated are regulated/adjusted by increasing or decreasing the current output settings on the motor 134, so that heated air is produced at a first predetermined temperature capable of inactivating the virus causing COVID-19 disease, (SARS-CoV-2) for a predetermined time and to promote an immunostimulatory response in the person.

However, because of safety controls built into, and/or associated with the heat gun 130 of FIG. 1A, the heat gun 130 does not have the first and second ball valves 48, 49 of the heat gun 30 of FIG. 1, which are deployed in the flexible heat resistant tubing 20 between the heat gun heat 30 and the CPAP-type face mask 10 of FIG. 1. Instead, the monitor controls of the control panel 141 regulate the heat and air pressure coming out of the heat gun 130 of FIG. 1A, and into the face mask 110 shown in FIG. 1A. The built-in and/or associated controls 141 of the heat gun 130 of FIG. 1A achieve the desired airflow and heated temperature of the air being delivered to the person through the CPAP-type mask 110.

The heat gun 130 of FIG. 1A is also capable of providing heated air from about 80° F. to 900° F., but in use, is limited to providing heated air at a minimum temperature of about 130° F., up to a maximum of about 300° F. These temperatures mimic the human tolerable temperatures of from about 130° F. to about 230° F. to which humans are exposed to in heated saunas. These elevated temperatures of heated air also contact the epithelial cells inside the throat and upper respiratory system of the patient, to which the SARS CoV-2 virus is attached and embedded within the epithelial cells of the patients upper and lower respiratory systems.

The predetermined temperature outputted by the heat gun 30 of FIG. 1 and the heat gun 30 of FIG. 1A, which may vary according to medical needs, initiates inactivation of the SARS CoV-2 virus causing COVID-19 disease, in the infected upper respiratory epithelial surfaces of the wearer. This threshold temperature can vary from typically about 80° F. to 300° F., preferably at least 132.8° F., up to about 230° F. when combined with a relative humidity, and at a tolerable air pressure mimicking air pressure to a respiratory obstructive/sleep apnea patient using analogously a CPAP machine. While normally CPAP machines treat obstructive respiratory conditions, such as sleep apnea, at a temperature of between 60 and 95° F., depending upon patient comfort. They generally are built to shut off at a 95° F. threshold.

Hence, for the treatment of COVID-19 disease caused by the SARS CoV-2 virus, the temperature should be a minimum of about 130° F., as evidenced in the Chan and WHO in vitro tests results, op cit, listed herein.

This elevated heat treatment which can vary in time from about a minimum of 15 minutes, up to 24 hours, as per medical instructions, is believed to have a synergistic effect on inactivation of the SARS CoV-2 virus, and hopefully a reduction in COVID-19 disease within the respiratory systems of the patient.

It is believed that humans can withstand breathing in sauna units, which are typically warmed to 176-230° F., therefore exposure of a COVID-19 or other patient to temperatures at or below sauna temperatures, but of about at least 130° F., can be medically acceptable.

Figure 2:
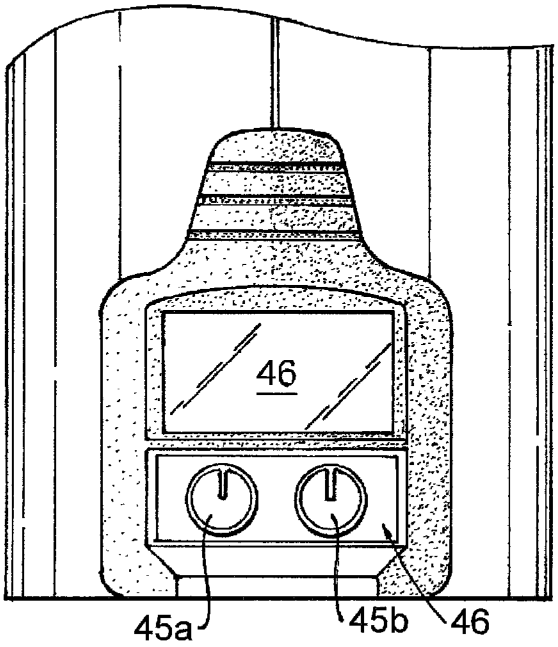
FIG. 2 is a top detail view of the heat gun of FIG. 1, taken at arrow "2" of FIG. 1, showing a display and control knobs, where, after the control knobs are turned to the appropriate heated air temperature and appropriate output air pressure, the locking key can set the predetermined air temperature and air pressure locked in place.

FIG. 2 shows a rear view of the heat gun of FIG. 1, taken at arrow "2" of FIG. 1, showing a control panel 41 with display 46 and control knobs 44. For use in provided heated air through a heat resistant flexible hose to a CPAP type face mask 10 covering the nose and mouth of the person, the temperature of the heated air from the heat gun 30, such as, for example, the Master Pro Heat gun model 1400, can also be set at a human tolerable upper limit, such as for example 200F or even 275° F., if medically appropriate, at air flow volumes of as little as 4 CFM (cubic feet per minute).

The rear of the heat gun handle 35 has ergonomic temperature and airflow controls, such as a pair of turnable knobs 45*a* and 45*b*, where one knob 45*a* is twisted and turned to adjust the airflow up or down to predetermined human tolerable levels, which are displayed in an LCD screen 46 above or adjacent to the knobs 45*a* and 45*b*. To adjust the temperature of the emitted air, the other knob 45*b* is twisted and turned to raise or lower the designated heat of the air flow output. A set temperature is displayed on the LCD screen 46 for several seconds, until the actual output air temperature is displayed on the LCD screen 46.

As also shown in FIG. 2, a further safety feature in the Master Pro Heat gun model 1400 is that adjacent to the two knobs 45*a*, 45*b* there is provided a locking lever or key 44*c*, typically, but not necessarily, magnetic, that is pushed or moved to set and lock the output air temperature and pressure. The settings inputted by the two knobs 45*a*, 45*b* cannot be changed if the LCD screen 46 indicates a "Lock" icon, due to the manipulation of the locking lever or key 44*c*. The locking lever or key 44*c* can alternatively be used for converting the temperature from Fahrenheit units to Celsius.

FIG. 3 shows a rear view of the heat gun 130 of FIG. 1A, taken at arrow "3" of FIG. 1A, showing a control panel 141 with display 146 and heat gun 130, such as the Master heat gun model 1500, also operates at 120/230 V AC, outgoing air temperatures can be as low as 130° F., extending up to 1000° F. The Master heat gun model 1500 also has a finger-operable ON/OFF switch on a trigger position of the handle, which has three setting depending upon selected movement of the switch. In a "HEAT" position, the top of the switch is depressed inward. To achieve a "COOL" position, the switch is set so that the top and bottom portions are equally extended. To turn the switch off, the bottom of the switch is completely pushed inward.

For use in provided heated air through a heat resistant flexible hose to a CPAP type face mask 110 covering the nose and mouth of the person, the Master Pro Heat gun model 1500 can also be set at a human tolerable upper limit, such as for example 200° F. or even 300° F., if medically appropriate, at air flow volumes of as little as 4 CFM (cubic feet per minute). The rear of the Model 1500 heat gun handle also has an LCD screen 146, but adjacent to, or below, the LCD screen 146 there is provided an array of programmable settings with keypad up/down arrow keys 144*a*, 144*b*, etc., where the one set of up and down arrow keys 144*a*, 144*b* are manipulated to adjust air pressure and another set of right up and down arrow keys 146*a*, 146*b* are manipulated to adjust the temperature up or down, to predetermined human tolerable levels, which are displayed in the LCD screen 146 above or adjacent to the key pad. In the middle between the left and right-side arrow keys are two other keys 144P, where the upper key has a "P" inscribed thereon, for programming the desired inputted air pressure and temperature outputs. The lower middle key 144 F/C is used to change the output levels from Fahrenheit to Celsius, or vice versa.

A further safety feature in the Master Pro Heat gun model 1500 is the programmable keys 144*a*, 144*b*, 146*a*, 146*b*, etc., can be used to set and lock the output air temperature and pressure. The settings inputted by the two knobs 44*a*, 44*b* of FIG. 1 or programmable keys 144*a*, 144*b*, 146*a*, 146*b* of FIG. 1A cannot be changed if locked by the key lock or by the programmable keys.

FIG. 3A is block diagram schematic of either of the heat guns of FIGS. 1 and 1A for providing respiratory therapy for COVID-19 patients, where breathing heated air at higher temperatures for longer periods is called for. An available heat source that is AC mains powered such as for example heat guns made by Master Pro Heat models 1400 and 1500 may be used. FIG. 3A is a high-level schematic that can describe both Master heat gun models 1400 and 1500 with adjustable airflow and temperature. These are microprocessor-controlled heat guns which sense airflow by monitoring blower motor rotational speed and use temperature feedback from reading the airflow temperature.

In FIG. 3A heat gun 30 of FIG. 1 uses microprocessor 132 to drive motor 134 through motor driver 136; it also drives heating elements 138 through driver 142. Electronic temperature sensor 124 reads effluent air temperature. Processor 132 also services the display 46 and the control panel 41 which serve as the person interface to set up operations. The same schematic applies to heat gun 130 of FIG. 1A.

Other safety features are in the Pro Heat model 1400, which is similar to heat gun 30 of FIG. 1. It uses a knob 45 on a potentiometer to set temperature as well as another knob 45 to set airflow velocity. A separate magnetic key 44*c* is inserted in either the airflow or the temperature keyhole to lock the values selected.

Figure 2A:
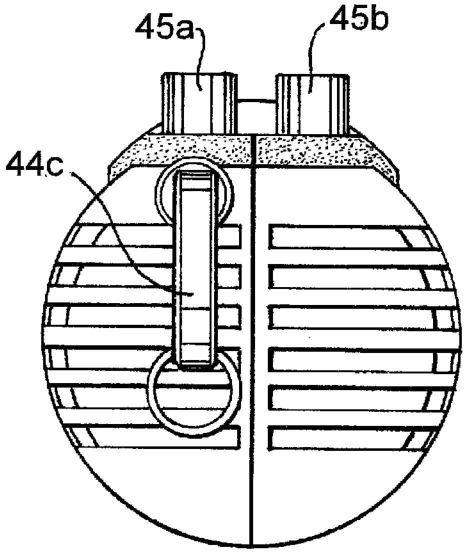
FIG. 2A is a close-up detail rear view of the control portion of the heat gun of FIG. 1.

The Pro Heat model 1500 is programmable; besides the modes of the model 1400, it can store 5 different pairs of airflow/temperature settings and can lock or unlock each of them without the use of a key, such as magnetic key 44*c* of FIG. 2A.

Figure 4:
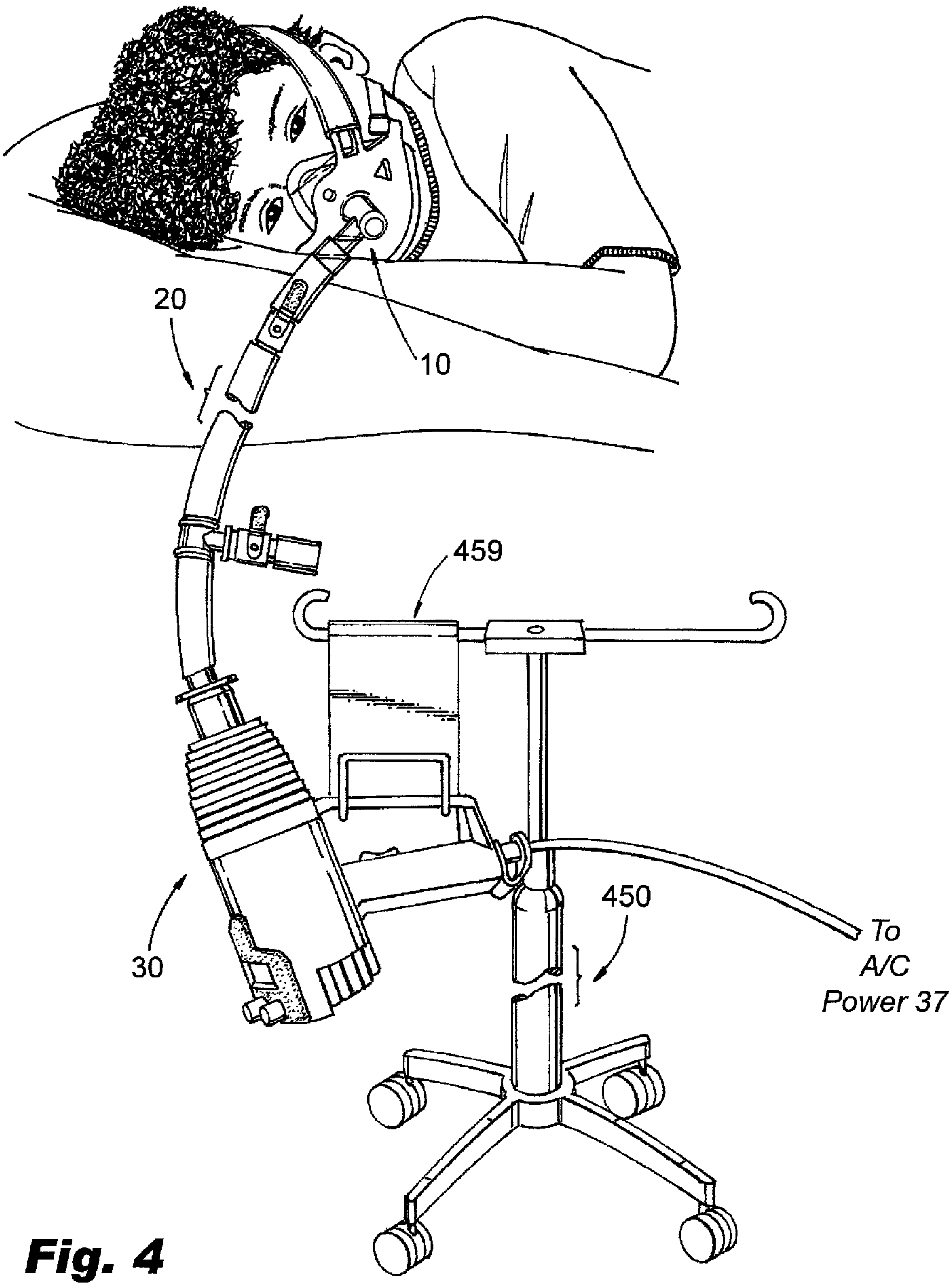
FIG. 4 is a perspective view of a child patient in bed, with a heat gun suspended on a rack, providing safe and needed heated temperature air, at an acceptably tolerable inhalation air pressure, through a flexible heat resistant conduit tube, to a heat mask covering the nose and mouth of the child patient.

FIG. 4 shows a child patient in bed, with a heat gun 30 suspended on a rack 459 on a movable hospital cart 450, providing safe and needed heated temperature air, at an acceptably tolerable inhalation air pressure, through a flexible heat resistant conduit tube 20, to a heat mask 10 covering the nose and mouth of the child patient. While the present invention can accommodate patients afflicted with COVID-19 lung disease, other respiratory diseases could also be treated, such as, for example, childhood cystic fibrosis. The bedridden child in the hospitalization setting is shown using the CPAP-type mask 10 attached by the flexible tube 20, wherein the heat gun 30 is capable of providing heated air in inhalation at predetermined high levels of heated air, in a humidified environment, for treatment of the upper respiratory system. and to promote an immunostimulatory response in the child or adult wearer.

Figure 5:
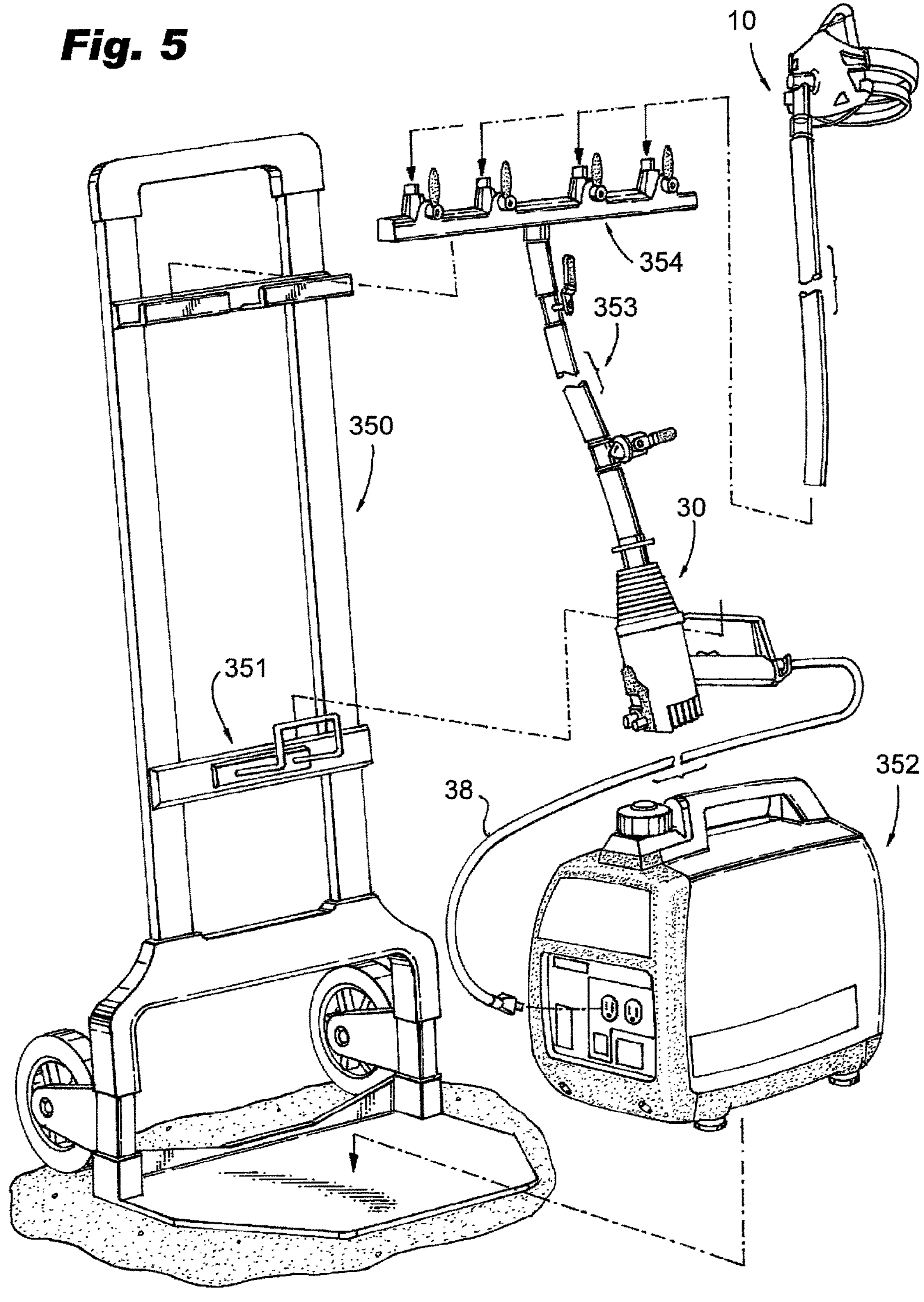
FIG. 5 is a perspective view of a hospital cart, having an optional generator, tube to a manifold, and having four face masks.

In a hospital setting, as shown in FIG. 5, a hospital cart 350 is shown, having an optional gasoline generator (Honda, EB22001TA) 352, tube 353 to a manifold 354, wherein the manifold 354 provides heated air at an appropriate air pressure to a plurality of face masks 10, such as, for example, four or more face masks 10, although up to ten or more face masks 10 can be accommodated by the manifold 354. The heat gun 30 can be installed on a rack 351 on the hospital cart 350, with an AC wall outlet or, optionally, to a Honda or other electrical generator 352 on the cart 350 for full ambulatory use (when in ventilated conditions to eliminate carbon monoxide), which lasts over eight hours at ¼ power. Generator 352 can last over three hours at full power, and by dividing the pressurized heated air from the manifold 354, can treat at least ten people with one heat gun 30. For example, the conversion of cubic feet per minute airflow (CFM) to liters per minute is 28.32; thus, a heat gun 30 sending heated pressurized air at 120° F. heat at 3.5 CFM, times the factor of 28.32=99.12 liters per minute. Since a human takes 5-8 liters at rest, therefore the present invention can bleed off 99.12 minus 8=91.12 liters per minute, for treating about ten persons people simultaneously.

In general, since the device is a medical device, optimally the heat guns have air temperature and air pressure controls, such as thermostats for temperature control, with automatic shutoff features and interlock. For example, the Master Pro Heat gun has a minimal air flow of cubic feet per minute (CFM) of 4 and a safety interlock built-in for temperature and air flow stopping. Converted to liters=0.28 Liters per minute, this is below the air flow of a human at rest with normal activities, which is about 5-8 liters per minute.

For example, while the heat guns may have finger operable keys for controlling air temperature and air pressure, optionally these person operable controls and shutoffs may have a fail-safe automatic shutoff and interlock preventing any heat output above a threshold maximum and preventing any air pressure above a threshold maximum, such as tolerated in a CPAP machine, to prevent accidental increases of temperatures and air pressures above what is tolerable in human respiration.

Figure 6:
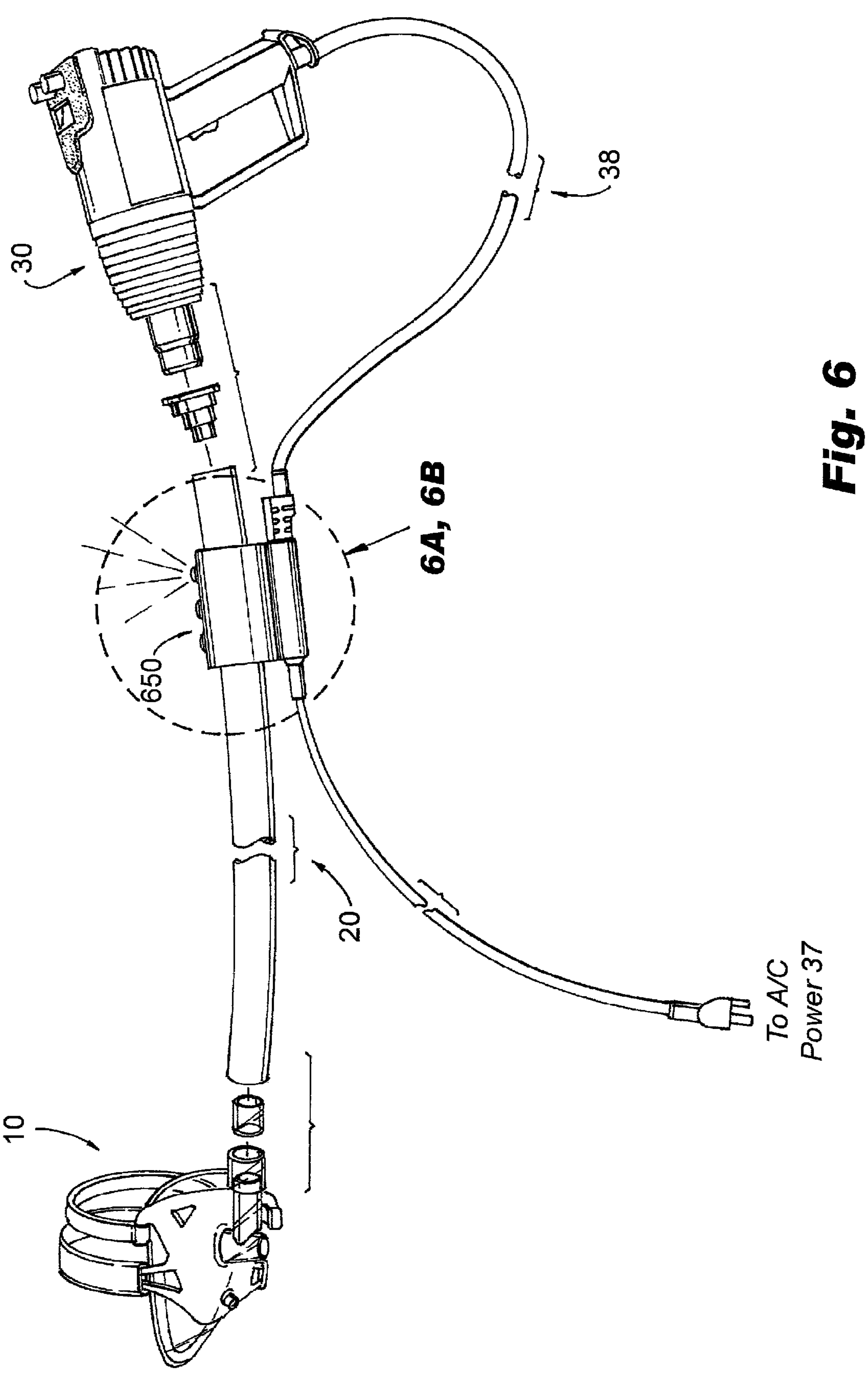

Therefore, as shown in the optional embodiment of FIGS. 6, 6A and 6B, since a heat gun is a powerful device which can deliver powerful airflow and temperatures up to 1000° F., it may be desirable in certain environments to optionally use a small safety plug-in interlock adapter 650, to separately monitor the temperature and pressure of the heated air delivered to a patient, and to shut down the system in case the built-in safety controls of the heat gun inadvertently fail due to human error or machine malfunction, whenever either the pressure or temperature in the patient hose exceed safety limits. A separate section of flexible tubing 20 or 120 is connected at one end to the collar adapter 650, and another section of the flexible tubing 20 or 120 is connected to the other end. The heated air flows through an internal tubing 651 of collar adapter 650, contacting thermal protection sensor switch 664 and air flow pressure sensor switch 666, sense any excessive temperature or air pressure in the heated air flow, due to human error or machine malfunctioning.

In general, in case of shut down, manual intervention (physically pressing the start button) is often required. Since the safety plug-in collar adapter 650 is plugged into the wall and the heat gun is plugged into the adapter, the heat gun need not be modified, but an extra degree of safety would be gained by having the line cord and plug of the heat gun fit into a mating outlet of the collar adapter to fit the keyed plug of the heat gun therein.

Such a simple interlock collar adapter 650 that is plugged into an AC outlet between the AC outlet and the AC compatible plug of the heat gun includes an AC relay, with normally open single pole contacts. An AC coil and related contacts make up a simple relay, which has separate ON and OFF momentary switches. One switch has normally open contacts and the other switch is in the relay latching circuit and it has normally closed contacts. The thermal sensor switch 664 with normally closed contacts is selected from a factory list of available temperatures. The maximum temperature selected must be above the range of operating temperatures. The normally closed pressure sensing switch 666 interfaces with the airflow to sense a pressure beyond operating region that is close to being a safety hazard. A fuse can complete the circuit. As also shown in FIGS. 6A and 6B, the optional safety plug-in interlock adapter 650 is a simple electromechanical design that is easy to understand and use. The principal component is optionally an AC relay 652 with normally open single pole contacts. AC coil 654 and contacts 656 comprise relay 652. It has separate ON 660 and OFF 662 momentary switches. Switch 660 has normally open contacts. Switch 662 is in the relay latching circuit and it has normally closed contacts. Switch 664 is a “Thermal Protect” sensor switch with normally closed contacts selected from a factory list of available temperatures. The temperature selected must be above the range of operating temperatures; perhaps 230° F. may be appropriate as a cut-off threshold air temperature. Switch 666 is a normally closed pressure sensing switch which is introduced into the airflow to sense a pressure beyond operating region that is close to being a safety hazard. Since a sensor switch at such low pressure may be difficult to purchase at a reasonable price one can be fabricated using a diaphragm or bellows and a snap action switch, high precision is not required. Indicator 668 and fuse 676 complete the circuit.

AC plug 674 of collar adapter 650 will fit the usual 120 VAC wall outlet. Plug-in outlet 670 mounted on adapter 650 is optionally keyed to prevent normal appliance plugs from mating. Keyed plug 672, connected to the heat gun 30 or 130, is designed to fit outlet 670.

The aforementioned optional simple plug-in interlock collar adapter 650 is a fail-safe shutoff to completely shut the heat gun down, if the heat gun itself has a malfunction in its operation or use.

As shown in FIG. 7, in a further alternate embodiment, an ambulatory person is shown using a cordless, portable, high temperature therapeutic heat gun heat 530, while preparing to don a CPAP-type mask 10, such as depicted in FIG. 1, attached by a flexible tube 20 having ball valves 48, 49 shown in FIG. 1, connected to the heat gun 530, which can be held by a belt 531*a* supported rack or holster 531. The cordless heat gun 530 is capable of providing heated air in inhalation at predetermined levels, at a reasonably low air pressure mimicking air pressure from a conventional CPAP machine in a humidified environment, to maintain the upper respiratory system infected by a resistant virus, such as, for example, the SARS-CoV-2 virus, at a further predetermined level, to deactivate the resistant virus and promote an immunostimulatory response in the wearer. In one therapy for ambulatory COVID-19 patients, breathing heated air for a relatively short period of time (such as 15 minutes at 130° F.) is helpful.

Figure 7A:
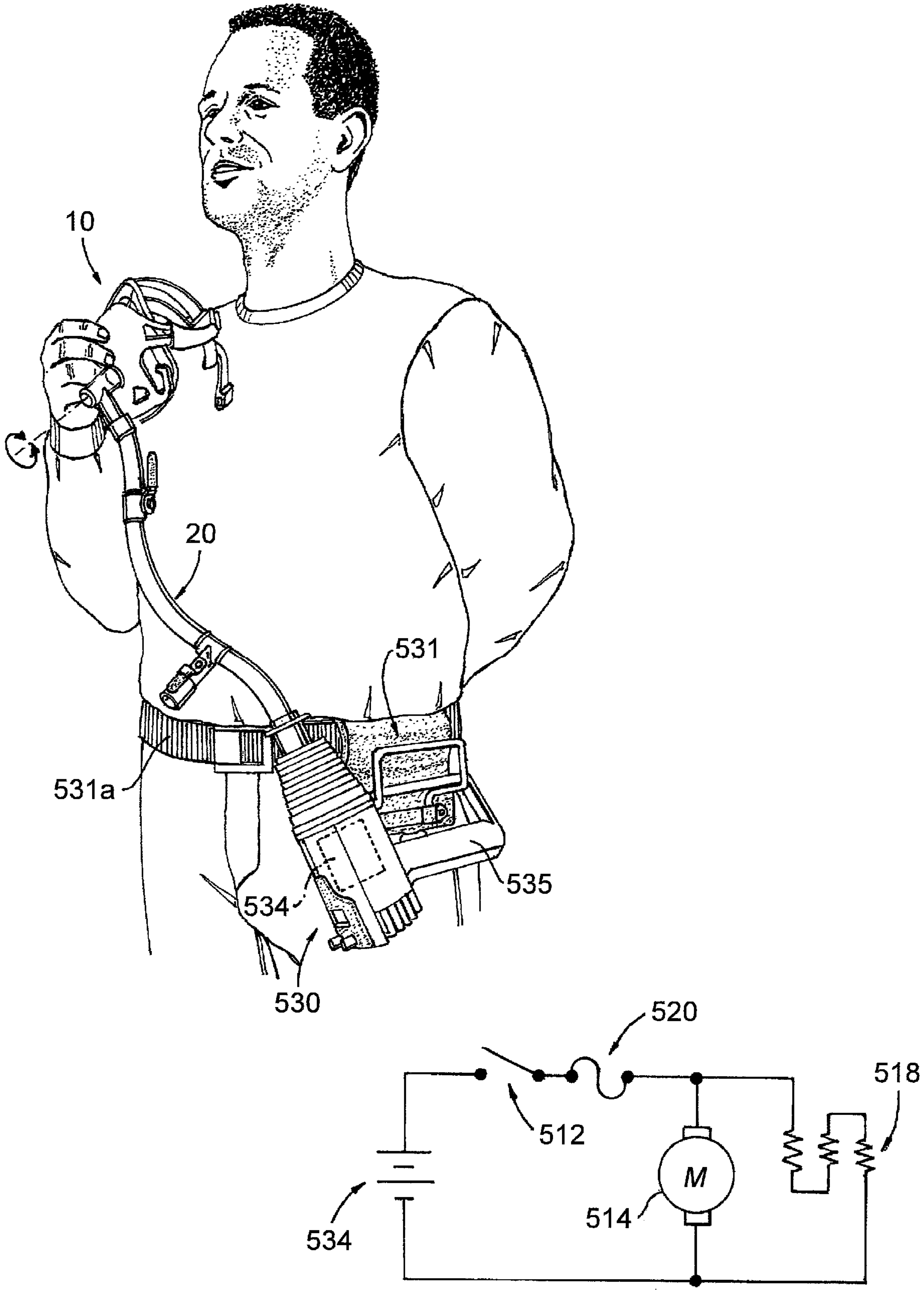
FIG. 7A is a schematic diagram of the cordless, portable, rechargeable heat source of FIG. 7.

FIG. 7 shows the purpose-built heat source 530 attached to patient mask 10 by a flexible tube 20. Compartment 532 of heat gun 530 houses a rechargeable battery 534, preferably lithium iodide. FIG. 7A is a schematic diagram for the portable, cordless heat gun embodiment of FIG. 7, showing battery 534, on/off switch 512, blower motor 514, and heating elements 518. These components are selected to inherently provide the desired mask pressure and temperature. Fuse 520 protects against over-current faults such as a short circuit. Because the design is limited by low voltage battery power (below hazard voltage) and a motor designed to blow about 8CMH20 pressure at 130 F, the heat source is intrinsically safe.

In the portable battery powered heat gun of FIG. 7, the wearer's belt accommodates heat gun 530 with low voltage (i.e., 12V or equivalent) battery 534, to provide electrical power to the heat gun 530 and its components, which are held within a belt holster or rack 531 on the wearer's belt 531*a*.

Preferably, in conclusion, as noted in drawing FIGS. 1-7A, in the therapeutic heat gun and face mask apparatus, the aforementioned heat source of the heat gun 30 or 130 has temperature and air pressure controls capable of maintaining the heated air above a minimal effective amount to inactivate a pathogen, such as the SARS Cov-2 virus, and below a second predetermined upper limit threshold temperature and air pressure for safe inhalation.

Besides treating SARS-CoV-2 induced COVID-19 disease, there is also provided a method of treating selected pathogens and lung diseases, selected from the group consisting of bacteria, viruses, fungi, asthma, mesothelioma, lung cancer, chronic obstructive pulmonary disease (COPD), emphysema, chronic bronchitis, pulmonary fibrosis, cystic fibrosis, pneumonia, heart disease and other cancers.

Preferably, the face mask heats air to a sufficiently high temperature is between about at least 80° F. and about 275° F., optionally, which said sufficiently high temperature is at least 132.8° F. at a relative humidity of from about 90% to about 95% relative humidity.

In order to keep the pressure of the heated air at a tolerable level compatible with human respiration, the air pressure of the heated air is compatible with typical air pressure flows in a Continuous Positive Air Pressure (CPAP) machine. Most CPAP machines pump air in the range from 6 to 15 cm/H20 (centimeters of water pressure), such as, for example, an air flow is set at 8 cm/H2O.

In the present invention, the heat gun 30, 130 or 530 must have the capability of providing heated air in the range of 80° F. to 275° F., preferably at sauna heat temperature levels of about 150 to 200° F. up to about 230° F., and at air pressure levels of no more than about 5.4 psi for human respiratory tolerance. While any heat gun which is capable of the aforementioned temperature and air pressure range limitations, non-limiting examples of such heat guns include the Master Pro Heat Gun models 1400 and 1500.

Besides being used for treatment of COVID-19 disease, heating the air passing through the heat chambers of the face masks disclosed in FIGS. 1-7A, can be done to raise the air temperature to a temperature and relative high humidity sufficiently high to destroy other selected pathogens within the respiratory system of the person. These include other selected pathogens and lung diseases which are selected from the group including bacteria, viruses, fungi, asthma, mesothelioma, lung cancer, dysplasia, chronic obstructive pulmonary disease (COPD), emphysema, chronic bronchitis, pulmonary fibrosis, cystic fibrosis, pneumonia, cancer in general, and heart disease, these alternate treatment regimens further preferably and optionally include the step of controlling the temperature, relative high humidity and elapsed time of the air being heated in the heat chamber by one of either a control box or an app on a smart phone, and providing a microprocessor for handling all communications and readings of a digital thermometer in the face mask.

It is further noted that the combination of providing heated pressurized air from heat guns through flexible tubing to face masks of FIGS. 1-7 can also be optionally used in a treatment method, stand alone, by itself, for cancers of the respiratory system, of augmenting cytotoxic chemotherapy, radiation, or immunotherapy for cancers of the lung, upper and lower respiratory tract and other body parts of a person, whereby heating the air passes through the aforementioned heat chambers to a temperature and relative high humidity sufficiently high to augment the cytotoxic chemotherapy or the immunotherapy and causes an immunological upregulation at the sites of the person being treated with the immunotherapy. These alternate treatment regimens also further preferably and optionally include the step of controlling the temperature, relative high humidity and elapsed time of the air being heated in the heat chamber by one of either a control box or an app on a smart phone, and providing a microprocessor for handling all communications and readings of a digital thermometer in the face mask.

Moreover, treatment of in situ cancers with isolated limb perfusion, is administered with a very high dose of chemotherapy, at elevated temperature, to isolated tumor sites without causing overwhelming systemic damage.

Also, heat can be combined with chemotherapy or radiation therapy to reduce or destroy cancer tumor cells, in combination with chemotherapy and/or radiation to destroy cancer cells and to enhance the anti-tumor effects of chemotherapy and/or radiation.

Likewise, Applicant's invention of delivering heated air through the mouth and nose of a cancer patient, can be used in combination with isolated limb perfusion cancer treatment and hyperthermia cancer treatment in general, because Applicant isolates his treatment to the respiratory tract, which is the primary site of COVID-19 disease and infection by the causative virus, (SARS-CoV-2), and administers a high dose of heated humidified air without causing overwhelming systemic damage."

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

What is claimed is:

1. A method of destroying a virus causing COVID-19 disease, (SARS-CoV-2) within the respiratory system of a person, comprising the steps of:

placing a mask on the face of said person, said mask comprising a housing mask covering the nose and mouth of said person;

connecting a heated air source to deliver ambient atmospheric air through a hose to said mask;

heating said air to a predetermined temperature exceeding activation temperature of the virus causing COVID-19 disease, (SARS-CoV-2) to destroy the virus causing COVID-19 disease, (SARS-CoV-2) in the person's respiratory system, said predetermined temperature being in a range of from about 130° F. to about 175° F.;

connecting a safety interlock in line with the hose, wherein the safety interlock separately monitors a temperature and a pressure of said delivered ambient atmospheric air from said heated air source via said hose and electrically disconnects the heated air source from a power source if said temperature or said pressure of said delivered ambient atmospheric air to said person exceed safety limits due to human error in set-up or to malfunctioning said heated air source.

2. The method of treating a virus causing COVID-19 disease as in claim 1, further comprising the steps of providing the heated air from a heat gun to upper and lower respiratory tracts of the person, at predetermined therapeutic thresholds of temperature air, pressure and exposure time duration, to the exact organs of SARS-CoV-2 infection, in the upper and lower respiratory tracts of the person, while sparing exposure to the rest of the body.

3. A therapeutic face mask apparatus for persons afflicted with the virus causing COVID-19 disease, (SARS-CoV-2) comprising:

a power source;

a heat source that provides adjustable heated and pressurized air for inhalation and td deliver ambient atmospheric air through a flexible conduit to a face mask;

said face mask worn over and covering the nose and mouth of a person;

said flexible conduit providing said heated and pressurized air to said person through said face mask, said heated and pressurized air is breathed in through said face mask during respiratory breathing of the person;

a safety interlock to separately monitor a temperature and a pressure of said heated and pressurized air delivered to said person via said flexible conduit, wherein the safety interlock is positioned in line with the flexible conduit, to electrically disconnect said power source from said heat source if said temperature or said pressure of said air delivered to said person exceed safety limits due to human error in set-up or to said heat source malfunction.

4. The therapeutic face mask apparatus as in claim 3 wherein said heat source has a temperature gauge monitoring temperature for adjustment of the amount of heat generating current to raise the heat to predetermined temperature to treat the person afflicted with the virus causing COVID-19 disease, (SARS-CoV-2);

wherein the air for inhalation by the person in said heat source is heated by an electrically resistive material contacting powered air from the heat source;

said temperature of said resistive material and of the heated air generated being regulated/adjusted by increasing or decreasing the current output settings on said power source, so that heated air is produced at a first predetermined temperature capable of inactivating the virus causing COVID-19 disease, (SARS-CoV-2) for a predetermined time.

5. The therapeutic face mask apparatus as in claim 3 wherein said heat source is a heat gun having temperature and air pressure controls capable of maintaining said heated air below a predetermined upper limit threshold of temperature and air pressure for safe inhalation.

6. The therapeutic face mask apparatus as in claim 5 wherein said heat source includes a switch wherein if said predetermined threshold temperature and air pressure for safe inhalation is exceeded, the heat gun will not operate and a visual display with display indicates an "OFF" mode.

7. The therapeutic face mask apparatus as in claim 5, wherein said heat gun is configured to deploy heated air in a range of from 80° F. to 300° F., for heating said air to a predetermined temperature exceeding activation temperature of the virus causing COVID-19 disease, (SARS-CoV-2) to destroy the selected pathogen virus causing COVID-19 disease, (SARS-CoV-2) in the person's respiratory system.

8. The therapeutic face mask apparatus as in claim 7, wherein said heat gun is configured to deploy heated air in a range of from 130° F. to 200° F., for heating said air to a predetermined temperature exceeding activation temperature of the virus causing COVID-19 disease, (SARS-CoV-2) high to destroy the selected pathogen virus causing COVID-19 disease, (SARS-CoV-2) in the person's respiratory system.

9. The therapeutic face mask apparatus as in claim 7, wherein said heat gun is configured to deploy heated air in a range of from 130° F. to 175° F., for heating said air to a predetermined temperature exceeding activation temperature of the virus causing COVID-19 disease, (SARS-CoV-2) high to destroy the selected pathogen virus causing COVID-19 disease, (SARS-CoV-2) in the person's respiratory system.

10. The therapeutic face mask apparatus as in claim 7, wherein said heat gun is configured to deploy heated air in a range of 105° F. to 300° F., for a period of time of about 15 minutes.

11. The therapeutic face mask apparatus as in claim 5, wherein said heat gun includes a lock for locking a predetermined temperature range and the range of air pressure between said first predetermined temperature and air pressure capable of inactivating the virus causing COVID-19 disease (SARS-CoV-2) and the second predetermined upper limit threshold temperature and air pressure for safe inhalation.

12. The therapeutic face mask apparatus as in claim 3 further comprising a lock locking a predetermined temperature range and said pressure between a first predetermined temperature and air pressure capable of inactivating the virus causing COVID-19 disease (SARS-CoV-2) and a second predetermined upper limit threshold temperature and air pressure for safe inhalation.

13. The therapeutic face mask apparatus as in claim 12 wherein said heat gun includes a keyboard capable of programing said first and second predetermined temperatures and air pressures.

14. The face mask of claim 3 which said power source is AC power transformed to a low voltage DC power source.

15. The face mask of claim 14 in which said power source is AC power.

16. The face mask of claim 3 in which said power source is a low voltage power source.

17. The face mask of claim 16 which said power source is a battery.

18. The therapeutic face mask apparatus of claim 3, wherein the safety interlock is built into a collar adapter plumbed between said heat source at an air input end and said flexible conduit at an air output end such that air delivered to said person by said face mask is sampled therein.

19. The therapeutic face mask apparatus of claim 18, wherein the safety interlock built into the collar adapter further comprises:

a thermal protector switch factory-set at a predetermined temperature safety limit;

a pressure sensing switch factory-set at the pressure safety limit;

an AC relay; and, an "ON" momentary push button.

20. A method of treating selected pathogens and lung diseases, selected from the group consisting of bacteria, viruses, fungi, mycoplasma, asthma, mesothelioma, lung cancer, dysplasia, chronic obstructive pulmonary disease (COPD), emphysema, chronic bronchitis, pulmonary fibrosis, cystic fibrosis, pneumonia, heart disease and breast, prostate, pancreatic, skin, non-Hodgkin lymphoma, kidney, thyroid, brain, endometrial leukemia, sarcoma, colorectal, gastrointestinal and lymphoma cancers, which metastasize from other sites to the lung, comprising the steps of:

placing a mask on the face of a person, said mask covering the nose and mouth of the person;

connecting a heated air source to deliver ambient atmospheric air through a hose to said mask; and, heating said air to a temperature exceeding activation temperature of the pathogen to destroy the selected pathogen;

connecting a safety interlock in line with the hose, wherein the safety interlock separately monitors a temperature and a pressure of said delivered ambient atmospheric air from said heated air source via said hose and electrically disconnects the heated air source from a power source if said temperature or said pressure of said delivered ambient atmospheric air to said person exceed safety limits due to human error in set-up or to malfunctioning said heated air source.

21. A method of augmenting cytotoxic chemotherapy, radiation or immunotherapy for cancers of the lung, upper and lower respiratory tract, and cancers of body parts of a person by supplying heated air to the person afflicted with said cancers of the lung, upper and lower respiratory tract, and cancers of body parts of a person, comprising the steps of:

placing a CPAP mask on the face of said person, said mask comprising a housing mask covering said nose and mouth of said person;

connecting a heated air source to deliver pure, ambient, atmospheric air through a hose to said CPAP mask;

heating said air to a temperature exceeding activation temperature of a pathogen, to destroy the selected pathogen in person's respiratory system; and wherein said heated air causes an immunological upregulation of immune stimulatory molecules, such as heat shock proteins, at the sites of the person being treated with said immunotherapy;

connecting a safety interlock in line with the hose, wherein the safety interlock separately monitors a temperature and a pressure of said delivered ambient atmospheric air from said heated air source via said hose and electrically disconnects the heated air source from a power source if said temperature or said pressure of said delivered ambient atmospheric air to said person exceed safety limits due to human error in set-up or to malfunctioning said heated air source.

* * * * *